US009243023B2

(12) United States Patent
Fang

(10) Patent No.: US 9,243,023 B2
(45) Date of Patent: Jan. 26, 2016

(54) PURIFICATION OF SYNTHETIC OLIGONUCLEOTIDES

(75) Inventor: Shiyue Fang, Houghton, MI (US)

(73) Assignee: MICHIGAN TECHNOLOGICAL UNIVERSITY, Houghton, MI (US)

( * ) Notice: Subject to any disclaimer, the term of this patent is extended or adjusted under 35 U.S.C. 154(b) by 97 days.

(21) Appl. No.: 13/876,201

(22) PCT Filed: Sep. 27, 2011

(86) PCT No.: PCT/US2011/053429
§ 371 (c)(1),
(2), (4) Date: Mar. 27, 2013

(87) PCT Pub. No.: WO2012/047639
PCT Pub. Date: Apr. 12, 2012

(65) Prior Publication Data
US 2013/0211065 A1  Aug. 15, 2013

Related U.S. Application Data

(60) Provisional application No. 61/386,799, filed on Sep. 27, 2010.

(51) Int. Cl.
| | | |
|---|---|---|
| C07H 21/00 | (2006.01) | |
| C07H 1/06 | (2006.01) | |
| C07H 19/073 | (2006.01) | |
| C07F 7/18 | (2006.01) | |
| C07F 9/22 | (2006.01) | |
| C07H 19/10 | (2006.01) | |
| C07H 23/00 | (2006.01) | |

(52) U.S. Cl.
CPC .............. *C07H 21/00* (2013.01); *C07F 7/1828* (2013.01); *C07F 9/222* (2013.01); *C07H 1/06* (2013.01); *C07H 19/073* (2013.01); *C07H 19/10* (2013.01); *C07H 23/00* (2013.01)

(58) Field of Classification Search
None
See application file for complete search history.

(56) References Cited

U.S. PATENT DOCUMENTS

| 3,712,936 | A | 1/1973 | Jelinek |
| 6,692,912 | B1 | 2/2004 | Boles et al. |
| 6,921,818 | B2 | 7/2005 | Sproat |
| 7,125,945 | B2 | 10/2006 | Shah |
| 2003/0096265 | A1 | 5/2003 | Brush et al. |
| 2003/0195351 | A1 | 10/2003 | Pieken |
| 2006/0178507 | A1 | 8/2006 | Berry et al. |
| 2008/0081902 | A1 | 4/2008 | Fang |

FOREIGN PATENT DOCUMENTS

| WO | WO 03/018616 | 3/2003 |
| WO | WO 2004/002995 | 1/2004 |
| WO | WO 2005/035588 | 4/2005 |
| WO | WO 2005/087818 | 9/2005 |
| WO | WO 2006/113792 | 10/2006 |
| WO | WO 2008/067026 | 6/2008 |
| WO | WO 2012/047639 | 4/2012 |

OTHER PUBLICATIONS

United States Patent Office Action for U.S. Appl. No. 12/966,396 dated Jun. 30, 2014 (13 pages).
Adamczyk, M. et al., "Synthesis of biological markers in fossil fuels. 2. Synthesis and 13C NMR studies of substituted indans and tetralins," J. Org. Chem. (1984) 49:4226-4237.
Atkinson, R.C. et al., "The syntheses and catalytic applications of unsymmetrical ferrocene ligands," Chem. Soc. Rev. (2004) 33:313-328.
Banfield, S.C. et al., "Unexpected reactivity of the Burgess reagent with thiols: synthesis of symmetrical disulfides," J. Org. Chem. (2007) 72(13):4989-4992.
Bondinell, W.E. et al., "Inhibitors of phenylethanolamine N-methyltransferase and epinephrine biosynthesis. 1. Chloro-substituted 1,2,3,4-tetrahydroisoquinolines," J. Med. Chem. (1980) 23:506-511.
Burgler. F.W. et al., "Stereoselective addition reactions with chalcogen electrophiles," Archive for Org. Chem. (2007) x:21-28.
Colacot, T.J., "A concise update on the applications of chiral ferrocenyl phosphines in homogeneous catalysis leading to organic synthesis," Chem. Rev. (2003) 103:3101-3118.
Crooke, S.T., "Progress in antisense technology," Annu. Rev. Med. (2004) 55:61-95.
Curnow, O.J. et al., "Facile meso to rac isomerization of the bisplanar chiral ferrocenyldiphosphine bis(1-(diphenylphosphino)-η5-indenyl)iron(II)," Organometallics (2002) 21:2827-2829.
Curnow, O.J. et al., "Mechanistic studies on a facile ring-flipping process in planar chiral ferrocenes under ambient and high pressure and its relevance to asymmetric catalysis," Organometallics (2004) 23:906-912.
Curnow, O.J. et al., "Synthesis, structures and rac\meso isomerization behaviour of bisplanar chiral bis(phosphino-η5-indenyl)iron(II) complexes," J. Organomet. Chem. (2004) 689:1897-1910.
Dai, L.X. et al., "Assymmetric catalysis with chiral ferrocene ligands," Acc. Chem. Res. (2003) 36:659-667.
Fang et al., "Scalable synthetic oligodeoxynucleotide purification with use of a catching by polymerization, washing, and releasing approach," Organic Letters, 21, Jul. 2010, 12:3720-3723.
Fang, S. et al., "Fluoride-cleavable biotinylation phosphoramidite for 5'-end-labeling and affinity purification of synthetic oligonucleotides," Nuc. Acids Res. (2003) 31(2):708-715.

(Continued)

*Primary Examiner* — Patrick Lewis
(74) *Attorney, Agent, or Firm* — Michael Best & Friedrich LLP

(57) ABSTRACT

This invention provides a method for purifying synthetic oligonucleotides comprising capping, polymerizing and separating any failure sequences produced during oligonucleotide synthesis. The invention also provides a method for purifying synthetic oligonucleotides comprising reacting a full length oligonucleotide with a compound to attach a polymerizable functional group to an end of the full length oligonucleotide, polymerizing the full length oligonucleotides and removing the failure sequences, and recovering the full length oligonucleotides. The invention also provides novel capping agents having a polymerizable functional group, and kits comprising at least one composition of the present invention.

6 Claims, 13 Drawing Sheets

(56) References Cited

OTHER PUBLICATIONS

Fang, S. et al., "Reversible 5'-end biotinylation and affinity purification of synthetic RNA," Tetrahedron Letters (2004) 45:7987-7990.
Fang, S. et al., "Reversible biotinylation of the 5'-terminus of ligodeoxyribonucleotides and its application in affinity purification," Curr. Protocols in Nucleic Acid Chem. (2003) 4.20.1-4.20.17.
Fang, S. et al., "Reversible biotinylation phosphoramidite for 5'-end-labeling, phosphorylation, and affinity purification of synthetic oligonucleotides," Bioconjugate Chem. (2003) 14:80-85.
Fang, S., "Simple methods for oligonucleotide purification," National Science Foundation Award Abstract #0647129 (2007) 2 pages—Retrieved from the Internet: http://www.nsf.gov/awardsearch/showaward.do?awardnumber=0647129, retrieved on May 6, 2008.
Farrugia, L.J., "ORTEP-3 for Windows—a version of ORTEP-III with a graphical user interface (GUI)," J. Appl. Cryst. (1997) 30:565.
Fu, G.C., "Asymmetric catalysis with 'planar-chiral' derivatives of 4-(dimethylamino)pyridine," Acc. Chem. Res. (2004) 37:542-547.
Gong, J-X. et al., "Total synthesis of gymnorrhizol, an unprecedented 15-membered macrocyclic polydisulfide from the Chinese mangrove Bruguiera gymnorrhiza," J. Org. Let. (2007) 9(9):1715-1716.
Hajipour, A.R. et al., "Oxidation of thiols with methyltriphenylphosphonium dichromate (MTPPD) in dichloromethane at room temperature," J. Sulfur Chem. (2006) 27(5):441-444.
Hauser, F.M. et al., "Ketone transposition: 2(1H)-tetralones from 1(2H)-tetralones," Synthesis-Stuttgart (1980) 621-623.
Imanishi, T. et al., "BNAs: novel nucleic acid analogs with a bridged sugar moiety," Chem. Commun. (2002) 1653-1659.
Ishikawa, F. et al., "Cyclic guanidines. XVI. Synthesis and biological activities of tetracyclic imidazo[2,1-b]quinazolinine derivatives," Chem. & Pharm. Bull. (1985) 33:3336-3348.
Ma, H.C. et al., "Synthesis of iminoquinones from anilines using IBX in DMSO," Synthesis (2007) 3:412-416.
Maier, T.C. et al., "Catalytic enantioselective O—H insertion reactions," J. Am. Chem. Soc. (2006) 128:4594-4595.
Olejnik, J. et al., "Photocleavable biotin phosphoramidite for 5'-end-labeling, affinity purification and phosphorylation of synthetic oligonucleotides," Nuc. Acids Res. (1996) 24(2):361-366.
Pearson, W.H. et al., "Fluorous affinity purification of oligonucleotides," J. Org. Chem. (2005) 70:7114-7122.
Ruble, J.C. et al., "Chiral π-complexes of heterocycles with transition metals: a versatile new family of nucleophilic catalysts," J. Org. Chem. (1996) 61:7230-7231.
Sathe, M. et al., "Oxidation of thiols to disulfides using silica chloride as heterogeneous catalyst," Chemistry Letters (2006) 35(9):1048-1049.
Schulte, M. et al., "Purification of DMT-on oligonucleotide by simulated moving-bed (SMB) chromatography," Org. Process Res & Dev. (2005) 9:212-215.
Shintani, R. et al., "Copper-catalyzed enantioselective conjugate addition of diethylzinc to acyclic enones in the presence of planar-chiral phosphaferrocene-oxazoline ligands," Org. Lett. (2002) 4:3699-3702.
Siemeling, U. et al., "1,1'-di(heteroatom)-functionalised ferrocenes as [N,N], [O,O] and [S,S] chelate ligands in transition metal chemistry," Chem. Soc. Rev. (2005) 34:584-594.
Sobik, P. et al., "Identification, synthesis, and conformation of tri- and tetrathiacycloalkanes from marine bacteria," J. Org. Chem. (2007) 72(10):3776-3782.
Sproat, B.S. et al., "Fast and simple purification of chemically modified hammerhead ribozymes using a lipophilic capture tag," Nuc. Acids Res. (1999) 27(8):1950-1955.
Trost, B.M. et al., "Asymmetric transition-metal-catalyzed allylic alkylations: applications in total synthesis," Chem. Rev. (2003) 103:2921-2943.
Trost, B.M., "Asymmetric catalysis an enabling science," Proc. Natl. Acad. Sci. USA (2004) 101:5348-5355.
Vester, B. et al., "LNC (Locked Nucleic Acid): High-affinity targeting of complementary RNA and DNA," Biochem. (2004) 43(42):13233-13241.
Wilson, C. et al., "Building oligonucleotide therapeutics using non-natural chemistries," Curr. Opin. Chem. Biol. (2006) 10:607-614.
Yavari, I. et al., "Conversion of thiols to disulfides using a hexamethylenetetramine-bromine complex," Phosphorus, Sulfur and Silicon and the Related Elements, (2006) 181(11):2659-2662.
Zhu et al. "An Aptamer Cross-Linked Hydrogel as a Colorimetric Platform for Visual Detection" Angew. Chem. Int. Ed., 2010, 49, 1052-1056.
International Search Report and Written Opinion of the International Searching Authority for Application No. PCT/US2007/080099 dated May 8, 2008 (12 pages).
United States Patent Office Action for U.S. Appl. No. 11/865,499 dated Jul. 8, 2009 (19 pages).
United States Patent Office Action for U.S. Appl. No. 11/865,499 dated Mar. 31, 2010 (22 pages).
United States Patent Office Action for U.S. Appl. No. 11/865,499 dated Aug. 10, 2010 (5 pages).
PCT/US2011/53429 International Search Report and Written Opinion dated Apr. 20, 2012 (13 pages).
United States Patent Office Final Rejection for U.S. Appl. No. 12/966,396 dated Dec. 3, 2014 (18 pages).
Choi, 2001, Angew. Chem. Int. Ed., 40, 1277-1279.

PURIFICATION OF SYNTHETIC OLIGONUCLEOTIDES

CROSS-REFERENCE TO RELATED APPLICATIONS

This application is a national stage filing under 35 U.S.C. 371 of International Application No. PCT/US2011/053429 filed Sep. 27, 2011, which claims the benefit of U.S. Provisional Patent Application Ser. No. 61/386,799, filed Sep. 27, 2010, which are incorporated by reference herein.

STATEMENT OF FEDERALLY SPONSORED RESEARCH OR DEVELOPMENT

This invention was made with government support under grant number CHE0647129 awarded by the National Science Foundation. The government has certain rights in the invention.

SEQUENCE LISTING

The instant application contains a Sequence Listing which has been submitted in text format via EFS-Web and is hereby incorporated by reference in its entirety. Said text copy, created on Mar. 21, 2013, is named 12708197ASFILED_SequenceListing-Text and is 712 bytes in size.

INTRODUCTION

Synthetic oligonucleotides have wide applications in biology and medicine. With one oligonucleotide drug on the market and many more in various stages of clinical trials, the interest in using oligonucleotides as therapeutic agents continues to grow. This increasing demand requires large quantities of oligonucleotides. For many purposes, including use as therapeutic agents to cure human diseases, these crude oligonucleotides must be purified to remove the failure sequences generated in the coupling steps in the synthesis. Currently used purification methods include gel electrophoresis, HPLC and others, all of which are expensive, labor intensive and unsuitable for large scale purification. The most frequently used purification methods such as gel electrophoresis are not suitable for large scale purification. Reverse phase and ion exchange HPLC have been adapted to large scale purification, but there are high costs associated with instrumentation, eluents (including their evaporation) and columns. Other known purification methods are also not ideal. Consequently, the development of highly efficient and low cost methods for large scale production of oligonucleotides is desired.

SUMMARY OF THE INVENTION

The present invention provides methods of purifying oligonucleotides. In some embodiments, the method of purifying an oligonucleotide comprises capping any failure sequences produced during synthesis with a capping agent comprising a polymerizable functional group, polymerizing the capped failure sequences, and separating the polymerized material from the full-length oligonucleotide. In other embodiments, the method of purifying an oligonucleotide comprises reacting a full length oligonucleotide with a capping agent comprising a polymerizable functional group, polymerizing the full length oligonucleotides, removing the failure sequences from the polymerized full length oligonucleotides, and recovering the full length oligonucleotides.

Accordingly, in one aspect, the invention features a method of purifying an oligonucleotide comprising capping any failure sequences produced during synthesis with a capping agent of formula (Ia), polymerizing the capped failure sequences, and separating the polymerized material from the full-length oligonucleotide, wherein the compound of formula (Ia) is:

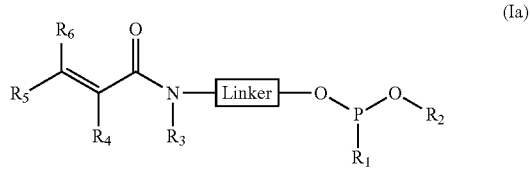

(Ia)

wherein:
$R_1$ is halo or $-NR_aR_b$;
$R_2$ is $-CH_3$ or $-CH_2-CH_2\text{-EWG}$;
EWG is an electron-withdrawing group;
$R_3$, $R_4$, $R_5$ and $R_6$ are each independently hydrogen or alkyl, wherein at least one of $R_4$, $R_5$ and $R_6$ is alkyl;
$R_a$ and $R_b$ are each independently alkyl;
linker is $(CH_2)_q$ or $(CH_2)_v[(CH_2)_v-O-(CH_2)_v]_p(CH_2)_v$ or $(CH_2)_v[(CH_2)_v-O-(CH_2)_v]_n(CH_2)_vN(R')C(=O)(CH_2)_m$ or $(CH_2)_nN(R')C(=O)(CH_2)_m$;
each v is independently an integer from 1 to 12;
q is an integer from 2 to 36;
p is an integer from 1 to 18;
n and m are independently an integer from 1 to 18; and
R' is hydrogen or alkyl group.

In another aspect, the invention features a method of purifying an oligonucleotide comprising capping any failure sequences produced during synthesis with a capping agent of formula (Ib), polymerizing the capped failure sequences, and separating the polymerized material from the full-length oligonucleotide, wherein the compound of formula (Ib) is:

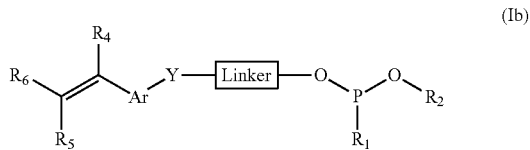

(Ib)

wherein:
Ar is arylenyl;
Y is $-O-$, $-CH_2-$, $-S-$, $-C(=O)N(R_7)-$, $-N(R_7)C(=O)-$ or $-N(R_7)-$;
$R_1$ is halo or $-NR_aR_b$;
$R_2$ is $-CH_3$ or $-CH_2-CH_2\text{-EWG}$;
EWG is an electron-withdrawing group;
$R_4$, $R_5$, $R_6$ and $R_7$ are each independently hydrogen or alkyl;
$R_a$ and $R_b$ are each independently alkyl;
linker is $(CH_2)_q$ or $(CH_2)_v[(CH_2)_vO(CH_2)_v]_p(CH_2)_v$ or $(CH_2)_v[(CH_2)_vO(CH_2)_v]_n(CH_2)_vN(R')C(=O)(CH_2)_m$ or $(CH_2)_nN(R')C(=O)(CH_2)_m$;
each v is independently an integer from 1 to 12;
q is an integer from 2 to 36;
p is an integer from 1 to 18;
n and m are independently an integer from 1 to 18; and
R' is hydrogen or alkyl group.

In another aspect, the invention features a method of purifying an oligonucleotide comprising:
reacting a full length oligonucleotide with a compound of formula (IIa) to attach a polymerizable functional group to an end of the full length oligonucleotide;
polymerizing the full length oligonucleotides;

removing the failure sequences from the polymerized full length oligonucleotides; and recovering the full length oligonucleotides, wherein the compound of formula (IIa) is:

(IIa)
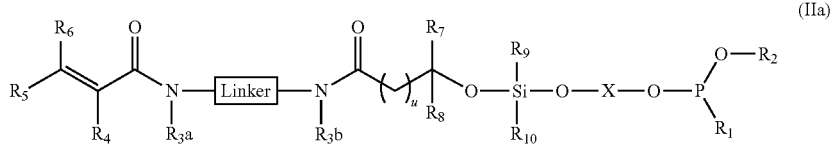

wherein:

X is selected from:

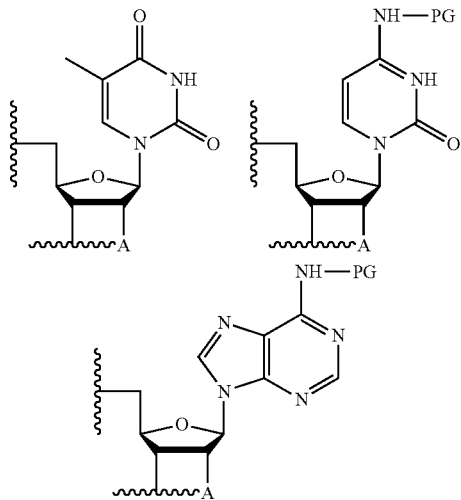

-continued

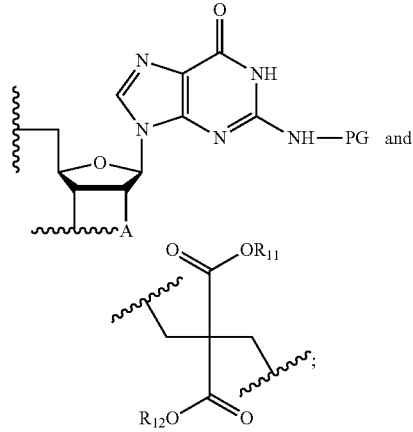

$R_1$ is halo or $-NR_aR_b$;

$R_2$ is $-CH_3$ or $-CH_2-CH_2$-EWG;

EWG is an electron-withdrawing group;

$R_{3a}$, $R_{3b}$, $R_4$, $R_5$ and $R_6$ are each independently hydrogen or alkyl;

$R_7$, $R_8$, $R_9$, $R_{10}$, $R_{11}$, $R_{12}$, $R_a$ and $R_b$ are each independently alkyl;

each A is independently selected from hydrogen and —O-PG;

each PG is independently selected from hydrogen and a protecting group;

linker is $(CH_2)_r$ or $(CH_2)_x[(CH_2)_xO(CH_2)_x]_p(CH_2)_x$;

each x is independently an integer from 1 to 12;

r is an integer from 1 to 36;

p is an integer from 1 to 18; and u is an integer from 0 to 34.

In another aspect, the invention features a method of purifying an oligonucleotide comprising:

reacting a full length oligonucleotide with a compound of formula (IIb), to attach a polymerizable functional group to an end of the full length oligonucleotide;

polymerizing the full length oligonucleotides;

removing the failure sequences from the polymerized full length oligonucleotides; and recovering the full length oligonucleotides, wherein the compound of formula (IIb) is:

(IIb)
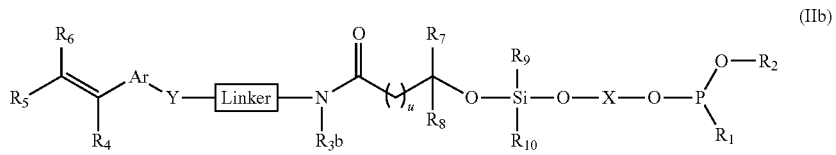

wherein:

X is selected from:

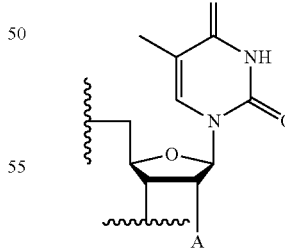

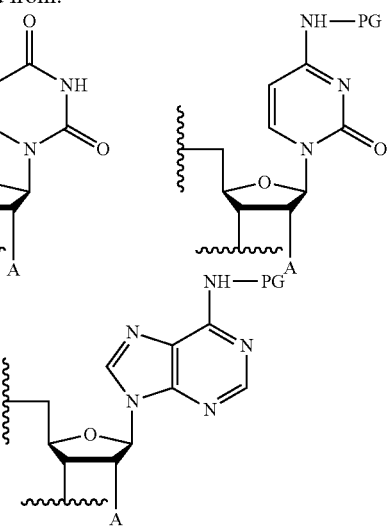

-continued

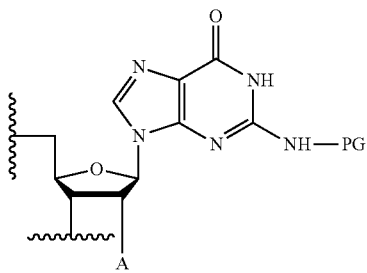
and

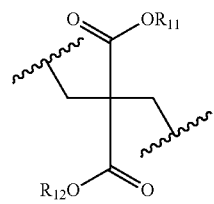
;

$R_1$ is halo or $-NR_aR_b$;
$R_2$ is $-CH_3$ or $-CH_2-CH_2-EWG$;
EWG is an electron-withdrawing group;
$R_{3b}$, $R_4$, $R_5$ and $R_6$ are each independently hydrogen or alkyl;
$R_7$, $R_8$, $R_9$, $R_{10}$, $R_{11}$, $R_{12}$, $R_{13}$, $R_a$ and $R_b$ are each independently alkyl;
Ar is arylenyl;
each A is independently selected from hydrogen and $-O-PG$;
each PG is independently selected from hydrogen and a protecting group;
Y is $-O-$, $-CH_2-$, $-S-$, $-C(=O)N(R_{13})-$; $-N(R_{13})C(=O)-$ or $-N(R_{13})-$;
linker is $(CH_2)_r$ or $(CH_2)_x[(CH_2)_xO-(CH_2)_x]_p(CH_2)_x$;
each x is independently an integer from 1 to 12;
r is an integer from 1 to 36;
p is an integer from 1 to 18; and
u is an integer from 0 to 34.

In another aspect, the invention features a method of purifying an oligonucleotide comprising:
reacting a full length oligonucleotide with a compound of formula (IIc), to attach a polymerizable functional group to an end of the full length oligonucleotide;
polymerizing the full length oligonucleotides;
removing the failure sequences from the polymerized full length oligonucleotides; and
recovering the full length oligonucleotides,
wherein the compound of formula (IIc) is:

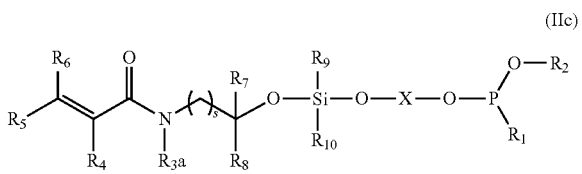
(IIc)

wherein:
X is selected from:

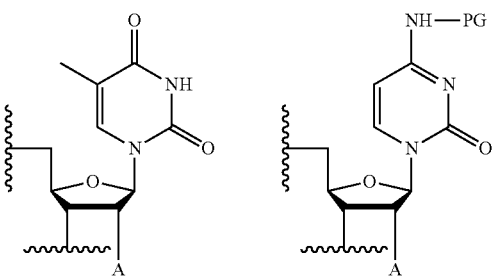

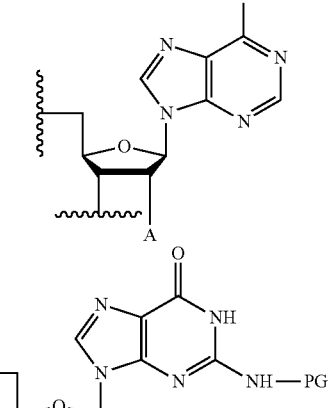
and

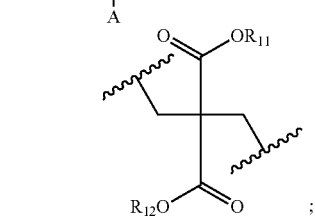
;

$R_1$ is halo or $-NR_aR_b$;
$R_2$ is $-CH_3$ or $-CH_2-CH_2-EWG$;
EWG is an electron-withdrawing group;
$R_{3a}$, $R_4$, $R_5$ and $R_6$ are each independently hydrogen or alkyl, wherein at least one of $R_4$, $R_5$ and $R_6$ is alkyl;
$R_7$, $R_8$, $R_9$, $R_{10}$, $R_{11}$, $R_{12}$, $R_a$ and $R_b$ are each independently alkyl;
each A is independently selected from hydrogen and $-O-PG$;
each PG is independently selected from hydrogen and a protecting group; and
s is an integer from 1-35.

In another aspect, the invention features a method of purifying an oligonucleotide comprising:
reacting a full length oligonucleotide with a compound of formula (IId), to attach a polymerizable functional group to an end of the full length oligonucleotide;
polymerizing the full length oligonucleotides;
removing the failure sequences from the polymerized full length oligonucleotides; and
recovering the full length oligonucleotides, wherein the compound of formula (IId) is:

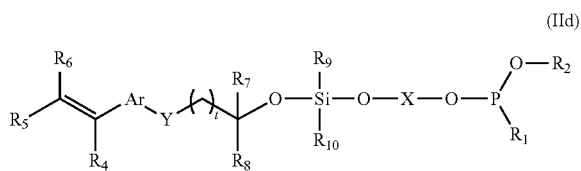

(IId)

wherein:
X is selected from:

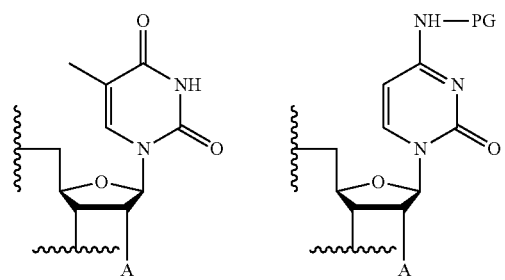

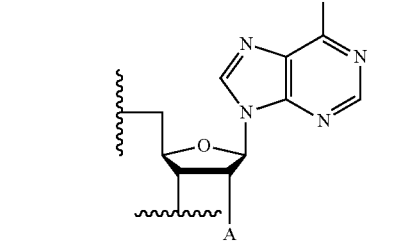

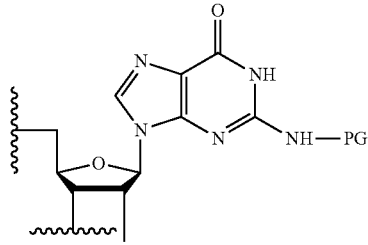

and

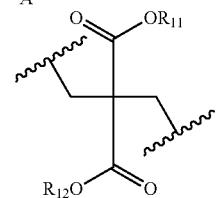

;

$R_1$ is halo or —$NR_aR_b$;
$R_2$ is —$CH_3$ or —$CH_2$—$CH_2$-EWG;
EWG is an electron-withdrawing group;
$R_4$, $R_5$ and $R_6$ are each independently hydrogen or alkyl;
$R_7$, $R_8$, $R_9$, $R_{10}$, $R_{11}$, $R_{12}$, $R_{13}$, $R_a$ and $R_b$ are each independently alkyl;
Ar is arylenyl;
Y is —O—, —$CH_2$—, —S—, —C(=O)N($R_{13}$)—; —N($R_{13}$)C(=O)— or —N($R_{13}$)—;
each A is independently selected from hydrogen and —O-PG;
each PG is independently selected from hydrogen and a protecting group; and
t is an integer from 0-35.

In another aspect, the invention features a method of purifying an oligonucleotide comprising:
reacting a full length oligonucleotide with a compound of formula (IIe) to attach a polymerizable functional group to an end of the full length oligonucleotide;
polymerizing the full length oligonucleotides;
removing the failure sequences from the polymerized full length oligonucleotides; and
recovering the full length oligonucleotides,
wherein the compound of formula (IIe) is:

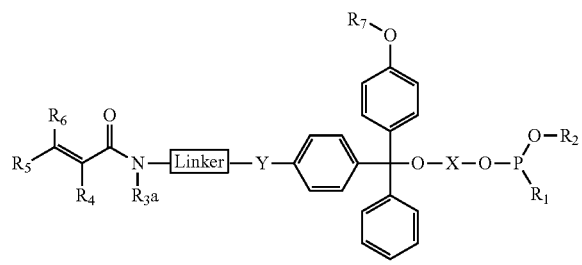

(IIe)

wherein:
X is selected from:

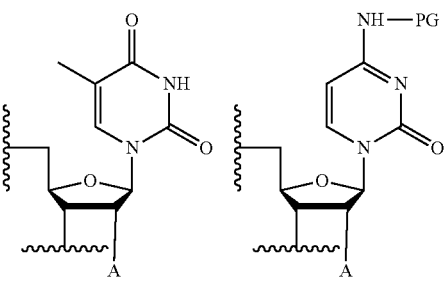

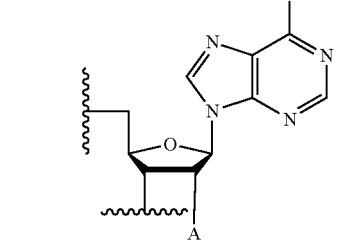

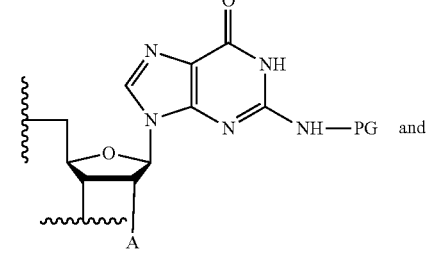

and

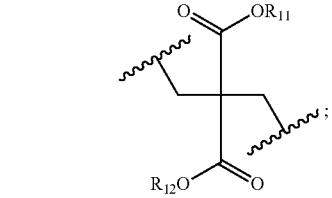

;

$R_1$ is halo or —$NR_aR_b$;
$R_2$ is —$CH_3$ or —$CH_2$-$CH_2$-EWG;
EWG is an electron-withdrawing group;

$R_{3a}$, $R_{3b}$, $R_4$, $R_5$, $R_6$ and $R_{20}$ are each independently hydrogen or alkyl;

$R_7$, $R_8$, $R_9$, $R_{10}$, $R_{11}$, $R_{12}$, $R_a$ and $R_b$ are each independently alkyl;

each A is independently selected from hydrogen and —O-PG;

each PG is independently selected from hydrogen and a protecting group;

Y is —O—, —CH$_2$—, —S—, —C(=O)N(R$_{20}$)—, —N(R$_{20}$)C(=O)— or —N(R$_{20}$)— linker is (CH$_2$)$_r$ or (CH$_2$)$_x$[(CH$_2$)$_x$O(CH$_2$)$_x$]$_p$(CH$_2$)$_y$ or (CH$_2$)$_x$[(CH$_2$)$_x$O(CH$_2$)$_x$]$_n$(CH$_2$)$_x$N(R')C(=O)(CH$_2$)$_m$ or (CH$_2$)$_r$N(R')C(=O)(CH$_2$)$_m$ or;

each x and y are independently an integer from 1 to 12;

r is an integer from 1 to 36;

p is an integer from 1 to 18; and m is an integer from 1 to 18.

In another aspect, the invention features a method of purifying an oligonucleotide comprising:

reacting a full length oligonucleotide with a compound of formula (IIf), to attach a polymerizable functional group to an end of the full length oligonucleotide;

polymerizing the full length oligonucleotides;

removing the failure sequences from the polymerized full length oligonucleotides; and recovering the full length oligonucleotides, wherein the compound of formula (IIf) is:

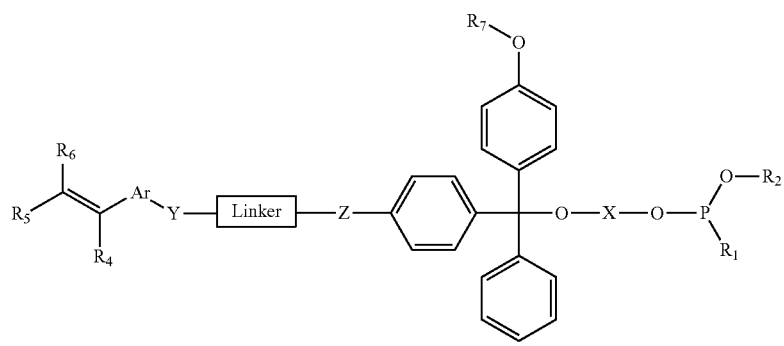

(IIf)

wherein:

X is selected from:

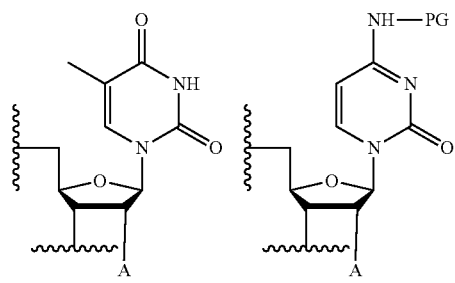

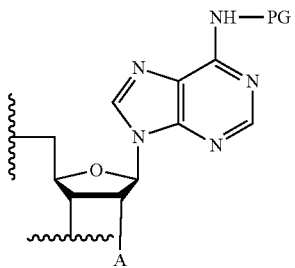

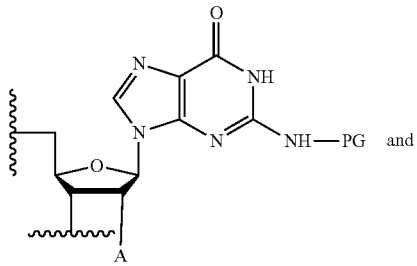

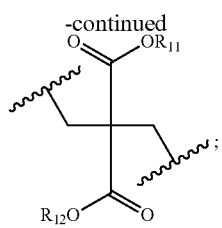

$R_1$ is halo or —NR$_a$R$_b$;

$R_2$ is —CH$_3$ or —CH$_2$—CH$_2$-EWG;

EWG is an electron-withdrawing group;

$R_{3b}$, $R_4$, $R_5$ and $R_6$ are each independently hydrogen or alkyl;

$R_7$, $R_8$, $R_9$, $R_{10}$, $R_{11}$, $R_{12}$, $R_{13}$, $R_a$ and $R_b$ are each independently alkyl;

Ar is arylenyl;

each A is independently selected from hydrogen and —O-PG;

each PG is independently selected from hydrogen and a protecting group;

each Z and Y are independently selected from —O—, —CH$_2$—, —S—, —C(=O)N(R$_{13}$)—; —N(R$_{13}$)C(=O)— or —N(R$_{13}$)—;

linker is (CH$_2$)$_r$ or (CH$_2$)$_x$[(CH$_2$)$_x$O(CH$_2$)$_x$]$_p$(CH$_2$)$_y$ or (CH$_2$)$_x$[(CH$_2$)$_x$O(CH$_2$)$_x$]$_n$(CH$_2$)$_x$N(R')C(=O)(CH$_2$)$_m$ or CH$_2$)$_r$N(R')C(=O)(CH$_2$)$_m$ or;

each x and y are independently an integer from 1 to 12;
r is an integer from 1 to 36;
p is an integer from 1 to 18; and
m is an integer from 1 to 18.

DETAILED DESCRIPTION OF THE INVENTION

Figure 1:
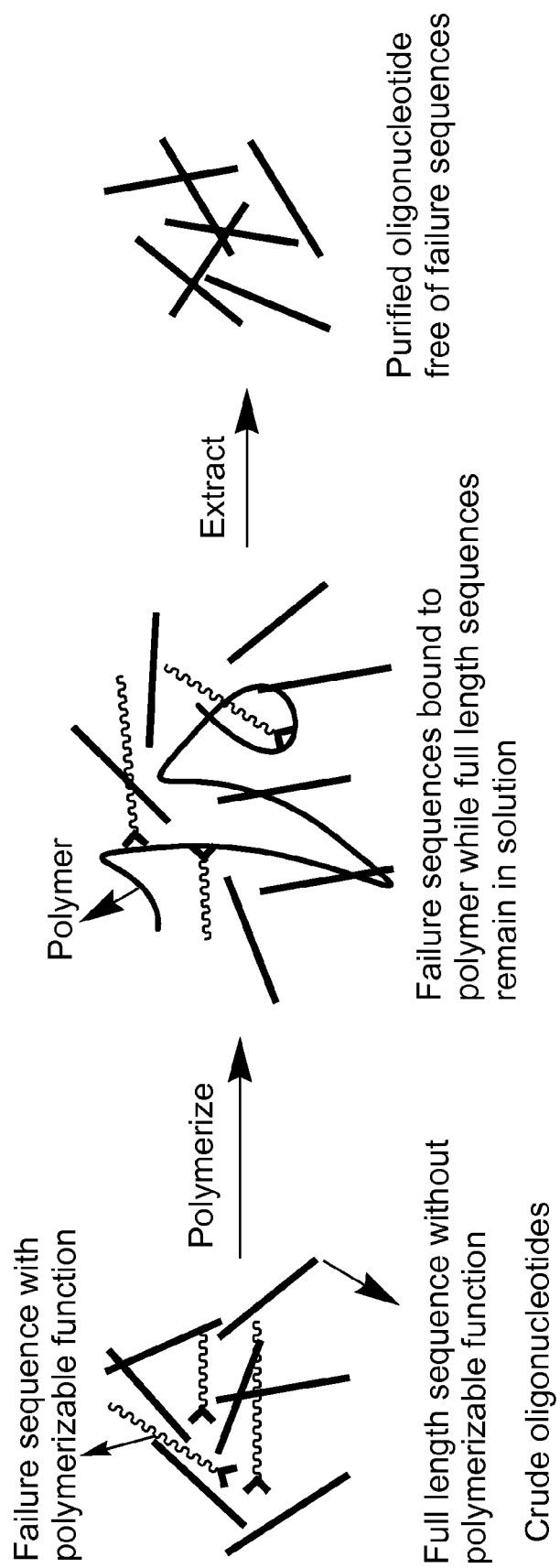
FIG. 1 illustrates one method for oligonucleotide purification. Unwanted failure sequences contain polymerizable functional groups, while the desired full length sequences do not. After polymerization, failure sequences are incorporated into a polymer, and full length sequences are isolated by simple extraction.

The present invention includes a method of purifying synthetic oligonucleotides via a polymerization technique, capping agents having a polymerizable functional group, and kits for purifying oligonucleotides comprising a capping agent having polymerizable functional group.

Synthesis of oligonucleotides generally proceeds in a stepwise manner with each monomer being added in sequence to the ends of a plurality of growing oligonucleotides. After synthesis and deprotection/cleavage, crude oligonucleotides normally contain the following impurities:

(i) Truncated failure sequences. These impurities result from the coupling steps of the synthesis. For a successful 20-mer synthesis, these impurities constitute about 30% of the oligonucleotide content of the crude mixture. They have similar physical properties as the desired full length sequences, and so are difficult to remove. They are usually capped with acetic anhydride during the synthesis. As a result, if the 5'-OH DMTr (4,4'-dimethoxytrityl) protecting groups in the last synthesis cycle are not removed, then after basic deprotection and cleavage, the full length sequences have the hydrophobic DMTr group on their 5'-end while the failure sequences do not (acyl groups on the failure sequences are removed under deprotection conditions). This is the basis of DMTr-on reverse phase HPLC purification. Although this is the most widely used oligonucleotide purification method, it is very costly for large scale production.

(ii) Small organic impurities. These result from the phosphate and exo-amino protecting groups which include acrylonitrile, benzamide, acetamide and isobutyramide and others depending on which protecting groups are used. Because of their very different physical properties from oligonucleotides, they can be simply removed by precipitation from aqueous buffer with butanol, ethanol or 2-propanol.

(iii) Other oligonucleotide impurities. These are very difficult to remove, and it is best to minimize the formation of these impurities by adjusting the synthesis conditions. Two examples are N+1 and N+2 sequences, which result from double coupling due to the mild acidity of activating agents that causes premature detritylation in the coupling step. They can be troublesome to remove even on small scale. When DMTr-on reverse phase HPLC is used, the impurities also contain a 5'-DMTr group. Ion-exchange HPLC cannot resolve a single nucleotide difference for a typical 20-mer. Gel electrophoresis can do the job but can only on a very small scale. Additional impurities are acrylonitrile-oligonucleotide adducts, which may be reversed to give unmodified ON by heating in concentrated NH$_4$OH. In addition, for oligophosphorothioate synthesis, impurities such as (P=O)$_1$ and (P=O)$_2$ mers exist, because of incomplete sulfurization. These impurities can be kept to a minimum amount by using a more efficient sulfurization agent.

The present invention contemplates the purification of oligonucleotides through the use of capping agents containing polymerizable functional groups. Failure sequences can be removed using the method of the present invention.

As used herein, the term "oligonucleotides" includes not only standard oligonucleotides but also modified oligonucleotides, polynucleotides and modified polynucleotides. Modified oligonucleotides and polynucleotides may include peptide nucleic acids, locked DNA and phosphorothioate oligonucleotides. One of ordinary skill in the art can envision other modified oligonucleotides and polynucleotides which fall within the scope of the present invention. The term "oligonucleotide" is not intended to be limited to any specific number of monomers. Instead, it is meant to encompass an oligonucleotide (or polynucleotide) of any length that can be made by a step-wise process.

As used herein, "failure sequence" means an oligonucleotide to which the next monomer did not attach during synthesis. Thus, a failure sequence of any given step in the synthesis contains all monomers except for the most recently added monomer.

As used herein, the term "alkyl" refers to a monovalent moiety obtained by removing a hydrogen atom from a hydrocarbon compound, which may be aliphatic or alicyclic, or a combination thereof, and which may be saturated, partially unsaturated, or fully unsaturated, and branched or unbranched. In some embodiments, the alkyl group has from 1 to 18 carbon atoms, or from 1 to 12 carbon atoms or 1 to 8 carbon atoms or 1 to 6 carbon atoms. As used herein, "lower alkyl" means an alkyl group of 1 to 4 carbon atoms. Exemplary lower alkyl groups include methyl, ethyl, propyl, iso-propyl, n-butyl, sec-butyl, iso-butyl and tert-butyl.

As used herein, the term "arylenyl" refers to a divalent moiety obtained by removing two hydrogen atoms from an aromatic ring atom of an aromatic compound, said compound having one ring, or two or more rings (e.g., fused), and wherein at least one of said ring(s) is an aromatic ring. Suitably, each ring has from 5 to 7 ring atoms. The ring atoms may be all carbon atoms. Examples of arylenyl groups that do not have ring heteroatoms include, but are not limited to, those derived from benzene (i.e. phenylenyl such as 1,4-phenylenyl), naphthalene, anthracene, phenanthrene, naphthacene and pyrene. Examples of aryl groups which have fused rings, one of which is not an aromatic ring, include, but are not limited to, groups derived from indene and fluorene. Alternatively, the ring atoms may include one or more heteroatoms, including but not limited to oxygen, nitrogen, and sulfur, as in "heteroarylenyl" groups. Examples of heteroarylenyl groups include, but are not limited to, those derived from furan, thiophene, pyrrole, imidazole, pyrazole, triazole, oxazole, isoxazole, thiazole, isothiazole, oxadiazole, tetrazole, oxadiazole, oxatriazole, isoxazine, pyridine, pyridazine, pyrimidine, pyrazine, triazine, benzofuran, isobenzofuran, indole, isoindole, benzothiophene, benzimidazole, quinoline, isoquinoline, benzodiazine, pyridopyridine, quinoxaline, carbazole, dibenzothiophene, dibenzofuran, acridine and phenazine.

As used herein, the term "halo" refers to a radical of fluorine, chlorine, bromine or iodine.

As used herein, the term "protecting group" refers to a moiety that prevents chemical reactions from occurring on the atom (e.g., an oxygen atom) to which it is attached. A protecting group must also be removable by a chemical reaction. Such groups are well known in the art and include those described in detail in Protecting Groups in Organic Synthesis, T. W. Greene and P. G. M. Wuts, 3rd edition, John Wiley & Sons, 1999, the entirety of which is incorporated herein by reference. In some embodiments, the protecting group may be one typically used in oligonucleotide synthesis. Examples of protecting groups include, but are not limited to, silyl groups such as t-butyldimethylsilyl (TBDMS) and t-butyldimethylsilyloxymethyl (TOM) groups, which are removable using fluoride.

As used herein, the term "electron-withdrawing group" refers to a chemical substituent that withdraws electrons from the chemical group to which it is attached. Examples of electron withdrawing groups include, but are not limited to, —CN, —$SO_3R$, —$CO_2R$, —CHO, —COR, —$NO_2$, —$CF_3$, —$CCl_3$, halo groups and the like, wherein each R is independently hydrogen or alkyl. In one embodiment, the electron withdrawing group is —CN.

The oligonucleotide purification methods of the present invention are suitable for both large and small scale purification. Oligonucleotides purified by the methods of the present invention are substantially free of failure sequences and have similar or better quality than those purified by DMTr-on reverse phase HPLC method. The purified oligonucleotide may be of greater than about 90% purity, or greater than about 95%, or greater than about 97%, or greater than about 99% or greater than about 99.5%. By "substantially free," it is meant that the oligonucleotide contains less than about 5% by weight of failure sequences, or less than about 3%, or less than about 1% or less than about 0.5%.

In one embodiment of the present invention, simple phosphorous compounds that contain functional groups capable of polymerizing in the presence of an initiator and/or a polymerization partner are used as capping agents (in place of a standard capping agent, e.g., acetic anhydride) during oligonucleotide synthesis to block failure sequences. Thus, all unwanted failure sequences contain the polymerizable functions, while the desired full length sequences do not. After synthesis, failure sequences are incorporated into a polymerized material, and the full length oligonucleotides remain in solution or in the polymer matrix and are separated from the polymerized material using any technique known to one of ordinary skill in the art including extraction with buffer and filtration. If the oligonucleotide is synthesized on a solid support, the oligonucleotide can be cleaved from the solid support prior to polymerization. (See FIG. 1).

Figure 2:
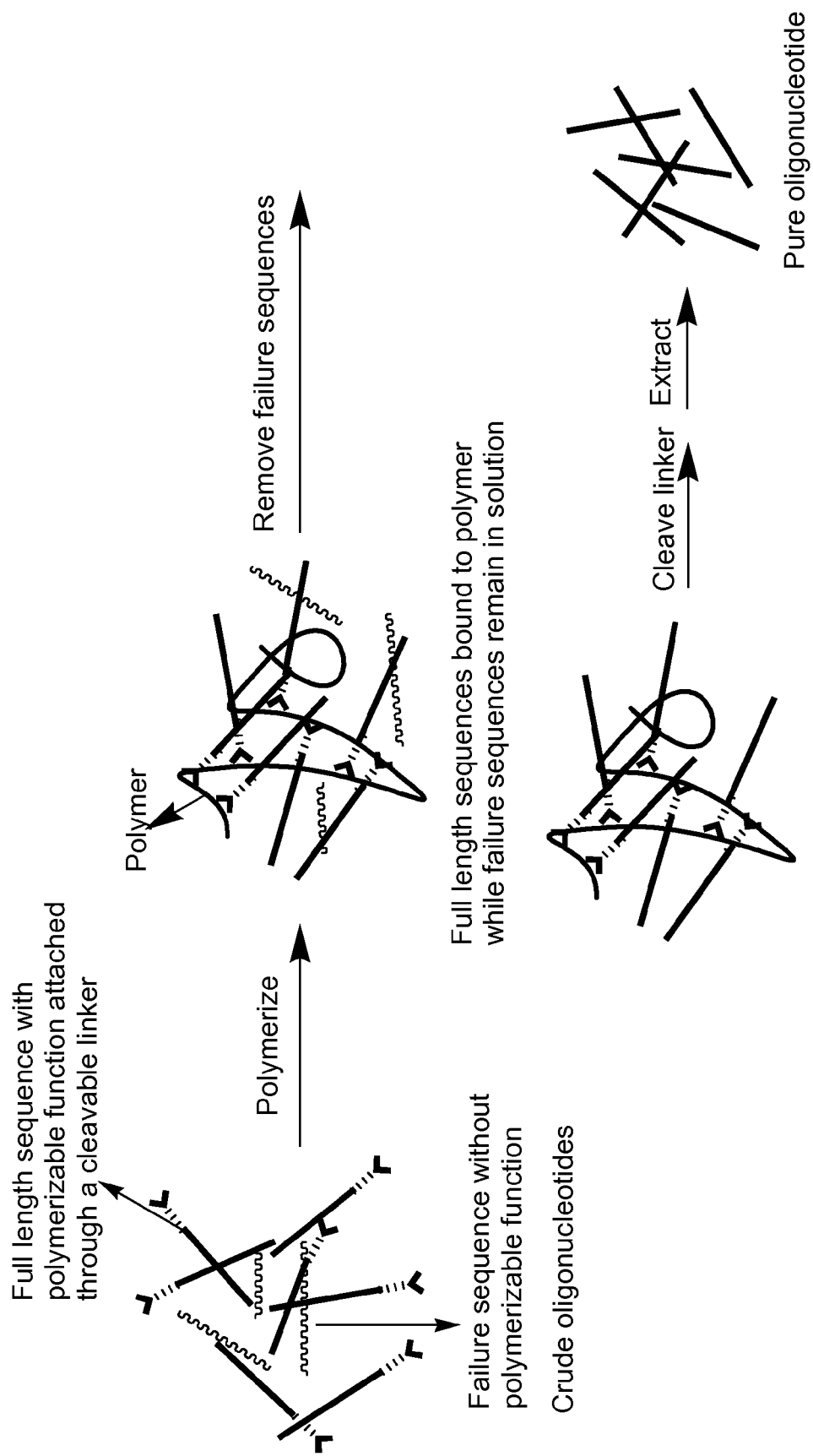
FIG. 2 illustrates an additional method for oligonucleotide purification. Desired full length sequences contain polymerizable function, while unwanted sequences do not. After polymerization, full length sequences are incorporated into a polymer, failure sequences are removed by washing, and full length sequences are cleaved from the polymer and extracted with a buffer.

In another embodiment of the present invention, a polymerizable functional group is incorporated onto the end of the full length sequence in the last step of oligonucleotide synthesis. Because failure sequences are capped with a standard capping agent, such as acetic anhydride, dimethylformamide, diethylene glycol monoethyl ether phosphoramidite, or bis(1,1,1,3,3,3-hexafluoro-2-propyl)-2-propyl phosphate in each synthetic cycle, only the full length sequence contains the polymerizable functional group. Once the full length sequences are incorporated into a polymerized material, the failure sequences are removed by simple washing because they do not contain a polymerizable functional group. The full length sequences are then recovered from the polymerized material using a cleavage reagent. (See FIG. 2).

Radical Acrylamide Polymerization

Figure 3:
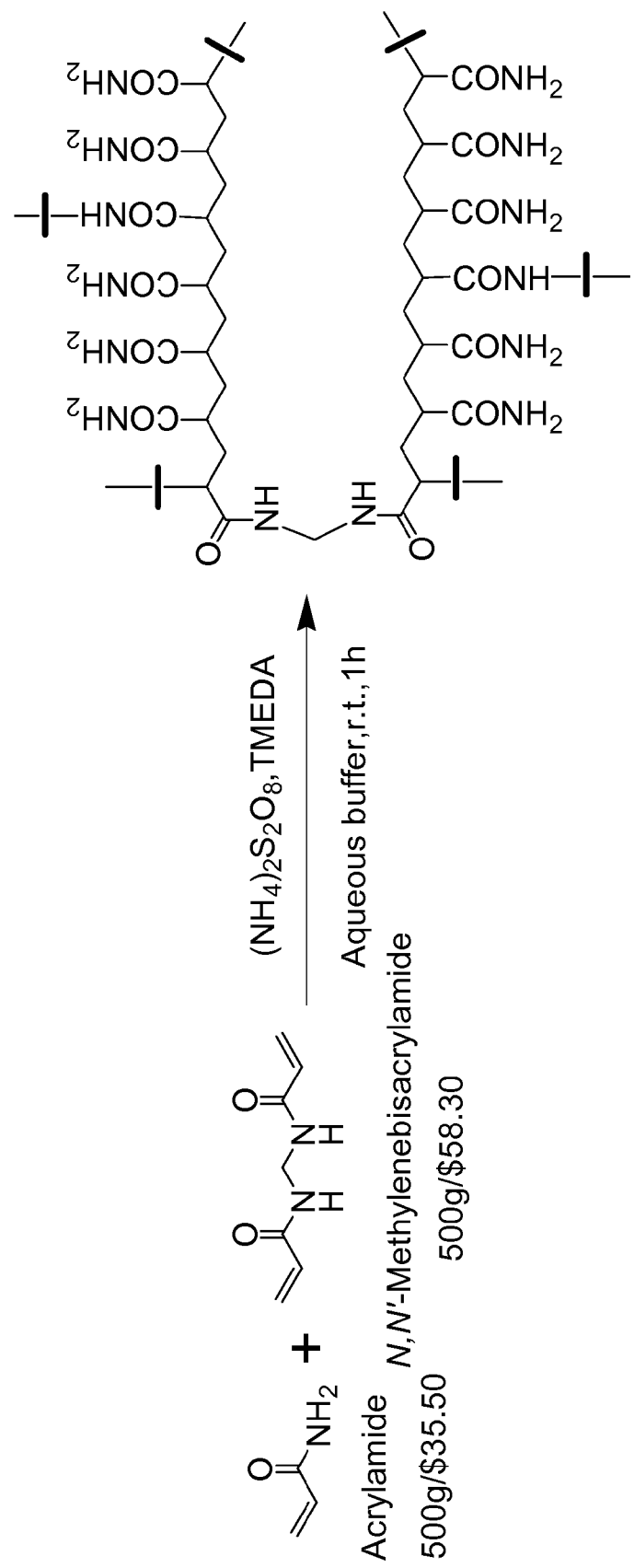
FIG. 3 represents the chemical reaction for formation of polyacrylamide gel.

The polymerization reaction used in the methods of the present invention is radical acrylamide polymerization. The general acrylamide polymerization reaction is shown in FIG. 3. The materials for this reaction are inexpensive, and the reaction is highly efficient and can be performed in aqueous buffer open to air at room temperature. In addition, acrylamide functionalities are stable under oligonucleotide synthesis and deprotection/cleavage conditions using phosphoramidite chemistry. Appropriate polymerization conditions can be readily determined by one of ordinary skill in the art. Suitable conditions include $(NH_4)_2S_2O_8$/TMEDA/water at room temperature for about 1 hour. For example, for a 1 mmol oligonucleotide synthesis, optionally about 10 mmol to about 100 mmol acrylamide, optionally about 0.2 mmol to about 2.0 mmol N,N'-methylene-bisacrylamide, about 1 μmol to about 10 μmol $(NH_4)_2S_2O_8$, and about 1 μmol to about 10 μmol TMEDA may be used.

Suitable capping agents for purification using radical acrylamide polymerization include compounds of formula (Ia-Id) shown below. For example, a compound according to formula (Ia) is suitable:

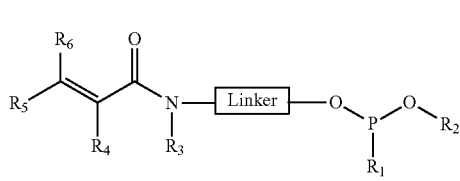

(Ia)

wherein:
$R_1$ is halo or —$NR_aR_b$,
$R_2$ is —$CH_3$ or —$CH_2$—$CH_2$-EWG;
EWG is an electron-withdrawing group;
$R_3$, $R_4$, $R_5$ and $R_6$ are each independently hydrogen or alkyl, wherein at least one of $R_4$, $R_5$ and $R_6$ is alkyl;
$R_a$ and $R_b$ are each independently alkyl; and
linker is $(CH_2)_q$ or $(CH_2)_v[(CH_2)_vO(CH_2)_v]_p(CH_2)_v$ or $(CH_2)_v[(CH_2)_vO(CH_2)_v]_n(CH_2)_vN(R')C(=O)(CH_2)_m$ or $(CH_2)_nN(R')C(=O)(CH_2)_m$;
each v is independently an integer from 1 to 12;
q is an integer from 2 to 36;
p is an integer from 1 to 18;
n and m are independently an integer from 1 to 18; and
R' is hydrogen or alkyl group.

Exemplary compounds according to formula (Ia) include:

In addition, compounds according to formula (Ib) are suitable:

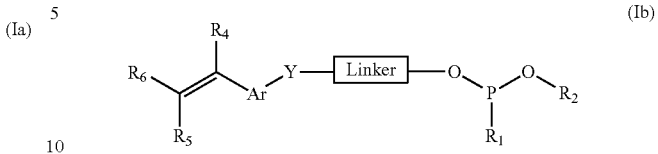

(Ib)

wherein:
Ar is arylenyl;
Y is —O—, —$CH_2$—, —S—, —C(=O)N($R_7$)—, —N($R_7$)C(=O)— or —N($R_7$)—;
$R_1$ is halo or —$NR_aR_b$,
$R_2$ is —$CH_3$ or —$CH_2$—$CH_2$-EWG;
EWG is an electron-withdrawing group;
$R_4$, $R_5$, $R_6$ and $R_7$ are each independently hydrogen or alkyl;
$R_a$ and $R_b$ are each independently alkyl;
linker is $(CH_2)_q$ or $(CH_2)_v[(CH_2)_vO(CH_2)_v]_p(CH_2)_v$ or $(CH_2)_v[(CH_2)_vO(CH_2)_v]_n(CH_2)_vN(R')C(=O)(CH_2)_m$ or $(CH_2)_nN(R')C(=O)(CH_2)_m$;
each v is independently an integer from 1 to 12;
q is an integer from 2 to 36;
p is an integer from 1 to 18;

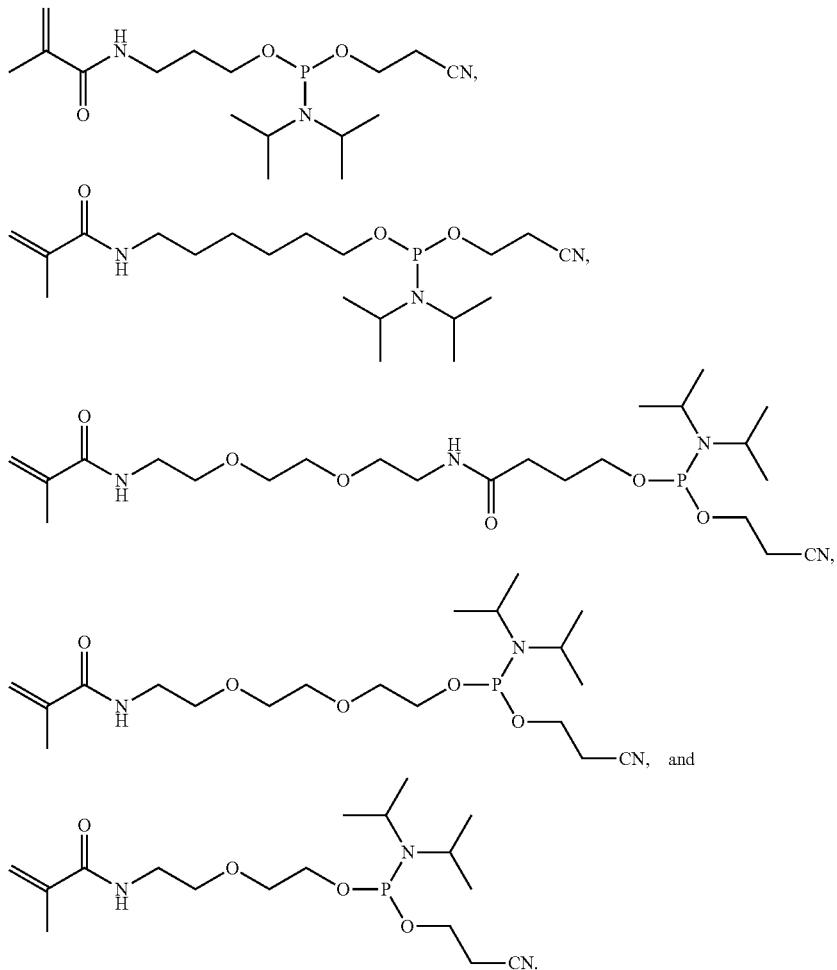

n and m are independently an integer from 1 to 18; and
R' is hydrogen or alkyl group.
Further, compounds of formula (Ic) are suitable:

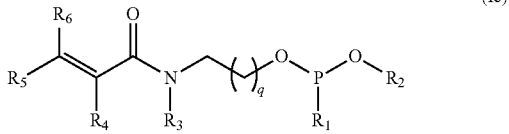
(Ic)

wherein:
$R_1$ is halo or $-NR_aR_b$,
$R_2$ is $-CH_3$ or $-CH_2-CH_2-EWG$;
EWG is an electron-withdrawing group;
$R_3$, $R_4$, $R_5$ and $R_6$ are each independently hydrogen or alkyl, wherein at least one of $R_4$, $R_5$ and $R_6$ is alkyl;
$R_a$ and $R_b$ are each independently alkyl; and
q is an integer from 2 to 36.
Exemplary capping agents of formula (Ic) include the following:

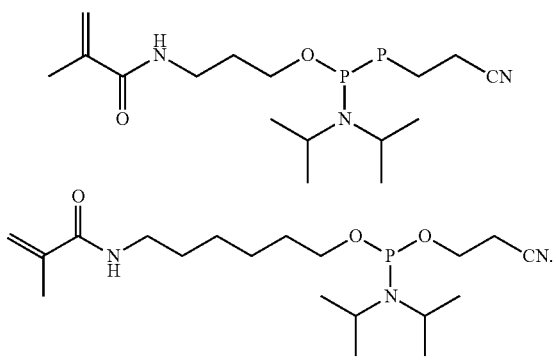

Additionally, compounds of formula (Id) are suitable:

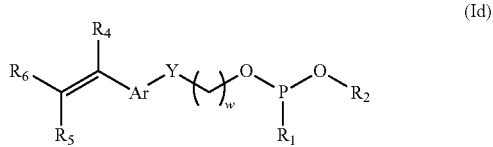
(Id)

wherein:
Ar is arylenyl;
Y is $-O-$, $-CH_2-$, $-S-$, $-C(=O)N(R_7)-$, $-N(R_7)C(=O)-$ or $-N(R_7)-$;
$R_1$ is halo or $-NR_aR_b$,
$R_2$ is $-CH_3$ or $-CH_2-CH_2-EWG$;
EWG is an electron-withdrawing group;
$R_4$, $R_5$, $R_6$ and $R_7$ are each independently hydrogen or alkyl;
$R_a$ and $R_b$ are each independently alkyl; and
w is an integer from 0 to 36.

When $R_1$ in any of the above formulae (Ia-Id) is $-NR_aR_b$ (i.e. a secondary amino group), the capping agents for radical acrylamide polymerization require the use of an activating agent. The most commonly used activating agent is 1H-tetrazole. Other suitable activating agents include, but are not limited to, 4,5-dicyanoimidazole, 5-(4-nitrophenyl)-1H-tetrazole, 5-methylthio-1H-tetrazole, 5-ethylthio-1H-tetrazole, ethylthiotetrazole, and 5-benzylmereapto-1H-tetrazole.

Optionally, when $R_1$ is a halogen atom, a base may be added to neutralize acid produced during the capping reaction. The base may be an amine base such as trimethylamine, pyridine, diazobicyclo base, or 5-methoxybenzimidazole.

Because there is less concern about premature detritylation in capping steps than in coupling steps, other phosphoramidite activators such as ammonium salts developed by Beaucage, Caruthers and Wada and co-workers can be used in the capping steps.

For purification of oligonucleotides using polyacrylamide formation reaction, an alternative procedure is to use a fluoride cleavable linker to attach the growing oligonucleotides to the solid support (instead of using the more common base cleavable linkers; besides fluoride cleavable linkers, other non-base cleavable linker such as photo cleavable linkers can also be used) for oligonucleotide synthesis. After synthesis, the oligonucleotides are cleaved from the solid support by treating with fluoride. The crude un-deprotected oligonucleotides are subjected to polymerization reaction conditions. The failure sequences are incorporated into a polymerized material and the full length sequences remain in solution or in polymer matrix. After removal of failure sequences by filtration and extraction of the full length sequences from polymer matrix, the full length sequences are subjected to base de-protection conditions and further purified by recrystallization to remove small molecules resulted from de-deprotection. This alternative purification procedure avoids the possibility of adding nucleophiles to acrylamide functionalities in the base de-protection steps.

Polymerization of Full Length Oligonucleotides

In another embodiment of the present invention, the polymerization reactions can be used to polymerize the desired full-length oligonucleotide sequence. In this embodiment, the capping agent is the normal acetic anhydride or any other suitable capping agent, but at the end of solid phase synthesis, a phosphoramidite that contains a suitable polymerizable functional group is coupled to the end of the oligonucleotide through a cleavable linker. Because failure sequences are all capped with acetic anhydride in each synthetic cycle, only the full length sequence contains the polymerizable functional group. After synthesis, deprotection and cleavage, the crude oligonucleotide is subjected to polymerization; the full length sequence is incorporated into the polymerized material while failure sequences and other impurities remain in solution, which can be removed by filtration or extraction with a buffer. The pure full length sequences are then cleaved from the polymerized material and extracted with a buffer.

Suitable phosphoramidites include compounds of formulas (IIa)-(IIh). Suitable phosphoramidites include compounds according to formula (IIa):

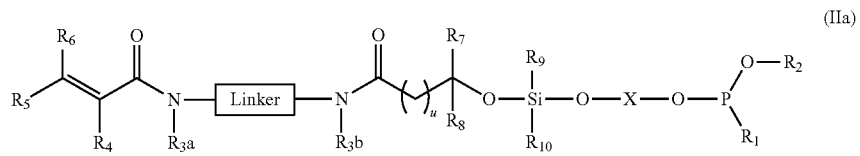
(IIa)

wherein:
X is selected from:

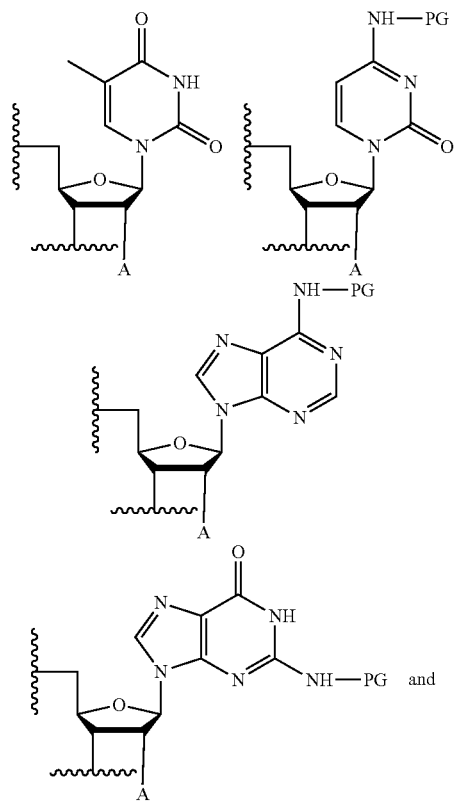

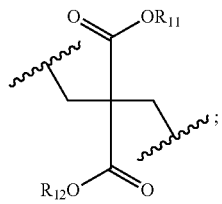

$R_1$ is halo or $-NR_aR_b$;

$R_2$ is $-CH_3$ or $-CH_2-CH_2$-EWG;

EWG is an electron-withdrawing group;

$R_{3a}$, $R_{3b}$, $R_4$, $R_5$ and $R_6$ are each independently hydrogen or alkyl;

$R_7$, $R_8$, $R_9$, $R_{10}$, $R_{11}$, $R_{12}$, $R_a$ and $R_b$ are each independently alkyl;

each A is independently selected from hydrogen and —O-PG;

each PG is independently selected from hydrogen and a protecting group;

linker is $(CH_2)_r$ or; $(CH_2)_x[(CH_2)_xO(CH_2)_x]_p(CH_2)_s$;

each s is independently an integer from 1 to 12;

r is an integer from 1 to 36;

p is an integer from 1 to 18; and u is an integer from 0 to 34.

Exemplary compounds according to formula (IIa) include:

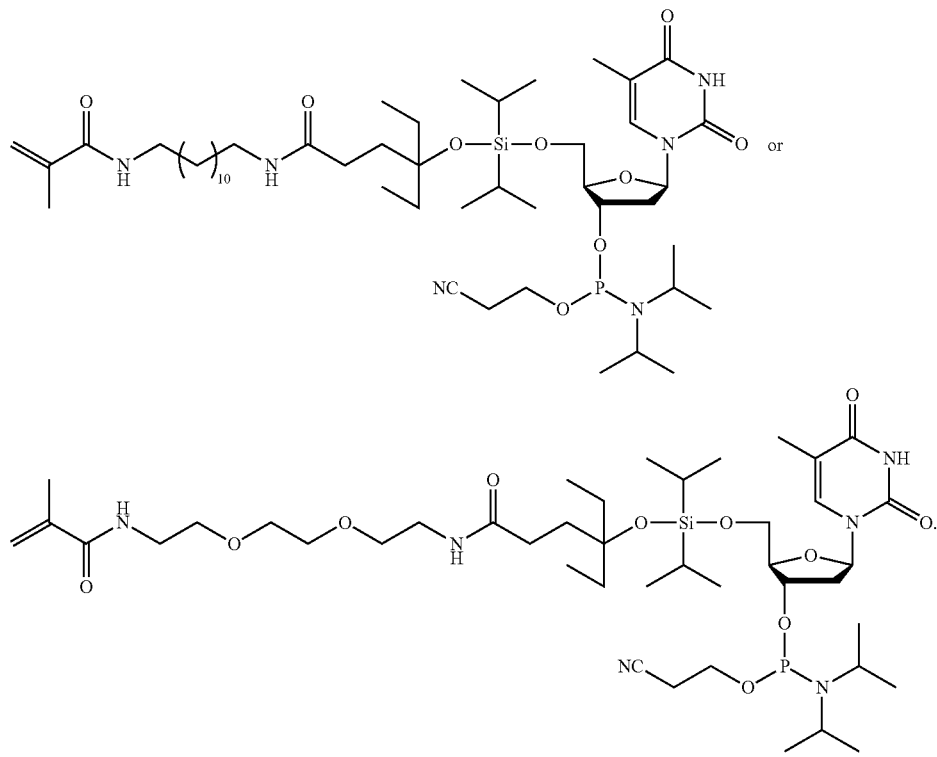

Suitable phosphoramidites additionally include compounds of formula (IIb):

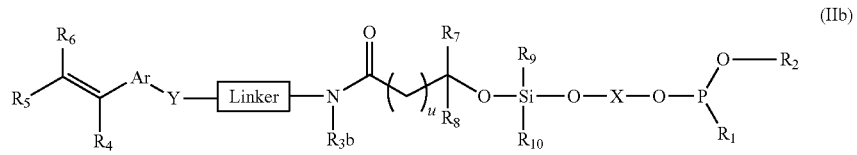

wherein:
X is selected from:

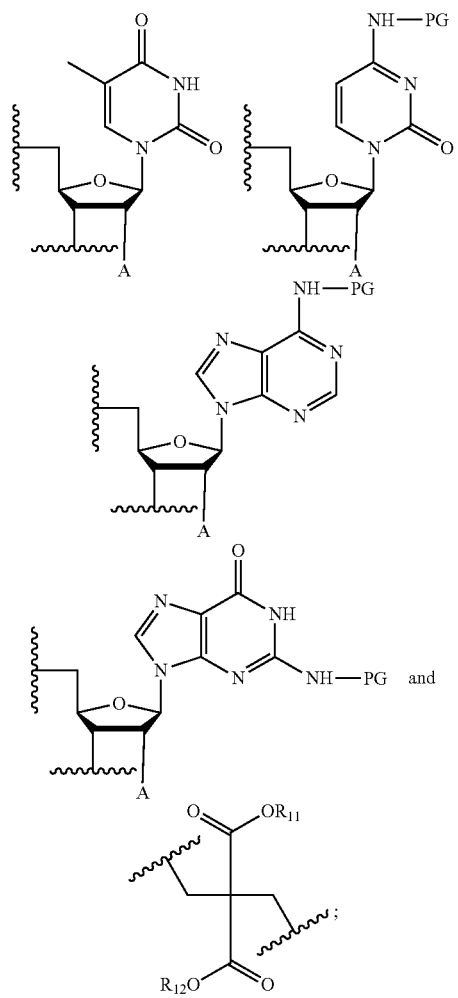

$R_1$ is halo or —$NR_aR_b$;
$R_2$ is —$CH_3$ or —$CH_2$—$CH_2$-EWG;
EWG is an electron-withdrawing group;
$R_{3b}$, $R_4$, $R_5$ and $R_6$ are each independently hydrogen or alkyl;
$R_7$, $R_8$, $R_9$, $R_{10}$, $R_{11}$, $R_{12}$, $R_{13}$, $R_a$ and $R_b$ are each independently alkyl;
Ar is arylenyl;
each A is independently selected from hydrogen and —O-PG;
each PG is independently selected from hydrogen and a protecting group;

Y is —O—, —$CH_2$—, —S—, —C(=O)N($R_{13}$)—; —N($R_{13}$)C(=O)— or —N($R_{13}$)—; linker is $(CH_2)_r$ or $(CH_2)_x[(CH_2)_xO(CH_2)_x]_p(CH_2)_x$;
each x is independently an integer from 1 to 12;
r is an integer from 1 to 36;
p is an integer from 1 to 18; and
u is an integer from 0 to 34.

Suitable phosphoramidites also include compounds of formula (IIc):

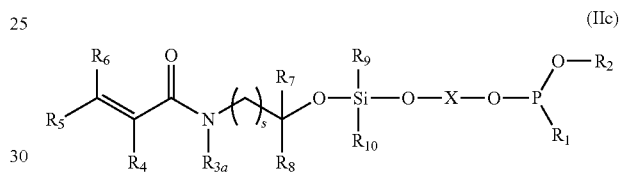

wherein:
X is selected from:

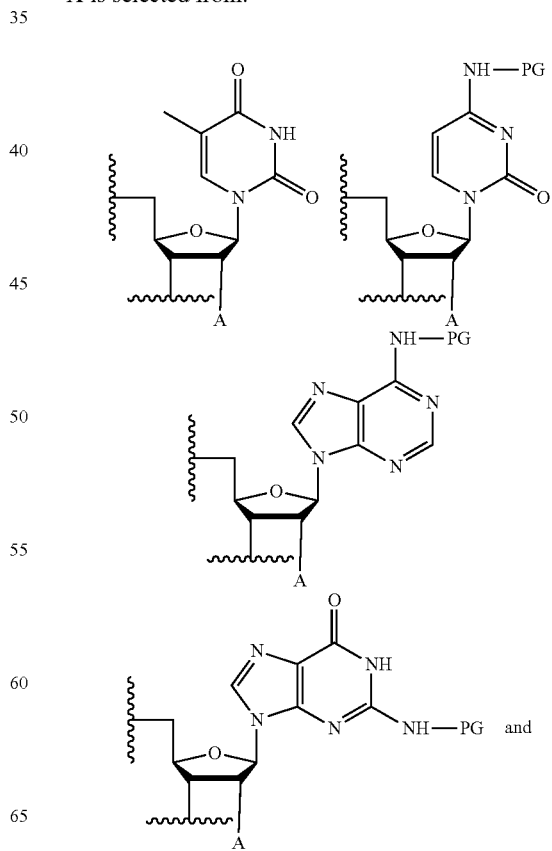

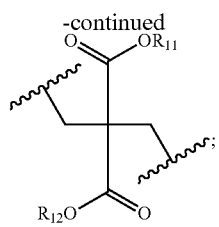

$R_1$ is halo or $-NR_aR_b$;
$R_2$ is $-CH_3$ or $-CH_2-CH_2-EWG$;
EWG is an electron-withdrawing group;
$R_{3a}$, $R_4$, $R_5$ and $R_6$ are each independently hydrogen or alkyl, wherein at least one of $R_4$, $R_5$ and $R_6$ is alkyl;
$R_7$, $R_8$, $R_9$, $R_{10}$, $R_{11}$, $R_{12}$, $R_a$ and $R_b$ are each independently alkyl;
each A is independently selected from hydrogen and $-O-PG$;
each PG is independently selected from hydrogen and a protecting group; and
s is an integer from 1-35.

Exemplary compounds according to formula (IIc) include:

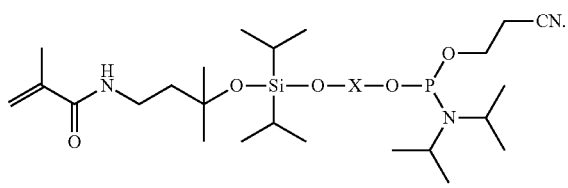

Suitable phosphoramidites also include compounds of formula (IId):

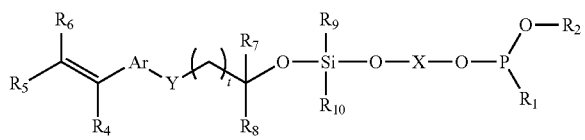

wherein:
X is selected from:

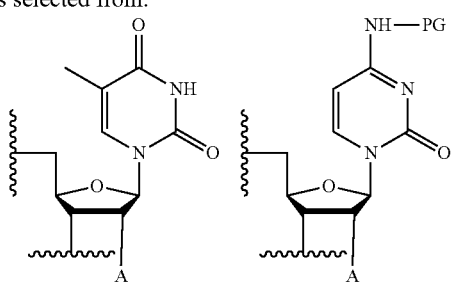

$R_1$ is halo or $-NR_aR_b$;
$R_2$ is $-CH_3$ or $-CH_2-CH_2-EWG$;
EWG is an electron-withdrawing group;
$R_4$, $R_5$ and $R_6$ are each independently hydrogen or alkyl;
$R_7$, $R_8$, $R_9$, $R_{10}$, $R_{11}$, $R_{12}$, $R_{13}$, $R_a$ and $R_b$ are each independently alkyl;
Ar is arylenyl;
Y is $-O-$, $-CH_2-$, $-S-$, $-C(=O)N(R_{13})-$; $-N(R_{13})C(=O)-$ or $-N(R_{13})-$;
each A is independently selected from hydrogen and $-O-PG$;
each PG is independently selected from hydrogen and a protecting group; and
t is an integer from 0-35.

Suitable phosphoramidites also include compounds of formula (IIe):

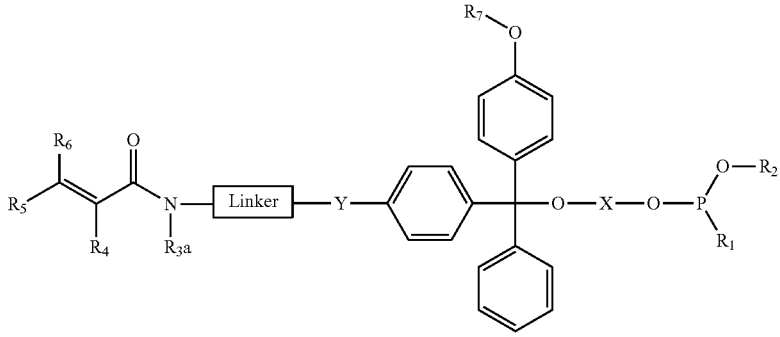

wherein:
X is selected from:

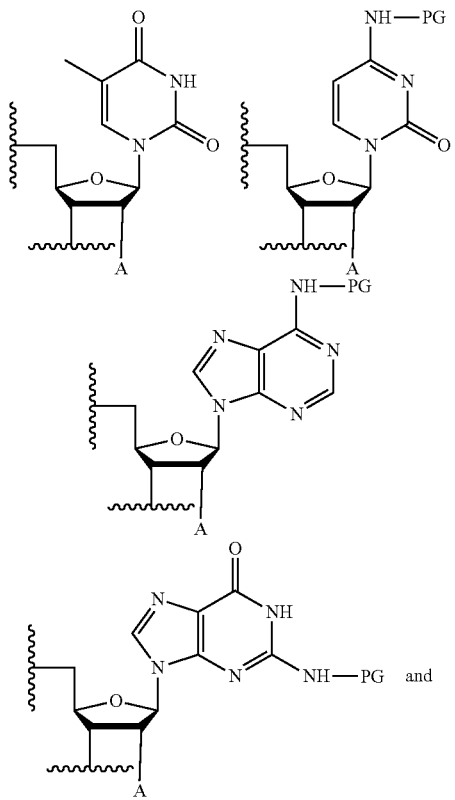

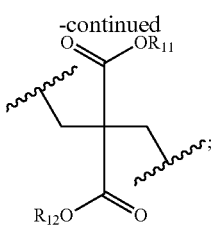

-continued $R_1$ is halo or $-NR_aR_b$;

$R_2$ is $-CH_3$ or $-CH_2-CH_2-EWG$;

EWG is an electron-withdrawing group;

$R_{3a}, R_{3b}, R_4, R_5, R_6$ and $R_{20}$ are each independently hydrogen or alkyl;

$R_7, R_8, R_9, R_{10}, R_{11}, R_{12}, R_a$ and $R_b$ are each independently alkyl;

each A is independently selected from hydrogen and $-O-PG$;

each PG is independently selected from hydrogen and a protecting group;

Y is $-O-$, $-CH_2-$, $-S-$, $-C(=O)N(R_{20})-$, $-N(R_{20})C(=O)-$ or $-N(R_{20})-$ linker is $(CH_2)_r$ or $(CH_2)_x[(CH_2)_xO(CH_2)_x]_p(CH_2)_y$ or $(CH_2)_x[(CH_2)_xO(CH_2)_x]_n(CH_2)_xN(R')C(=O)(CH_2)_m$ or $CH_2)_xN(R')C(=O)(CH_2)_m$ or;

each x and y are independently an integer from 1 to 12;

r is an integer from 1 to 36;

p is an integer from 1 to 18; and m is an integer from 1 to 18.

Exemplary compounds according to formula (IIe) include:

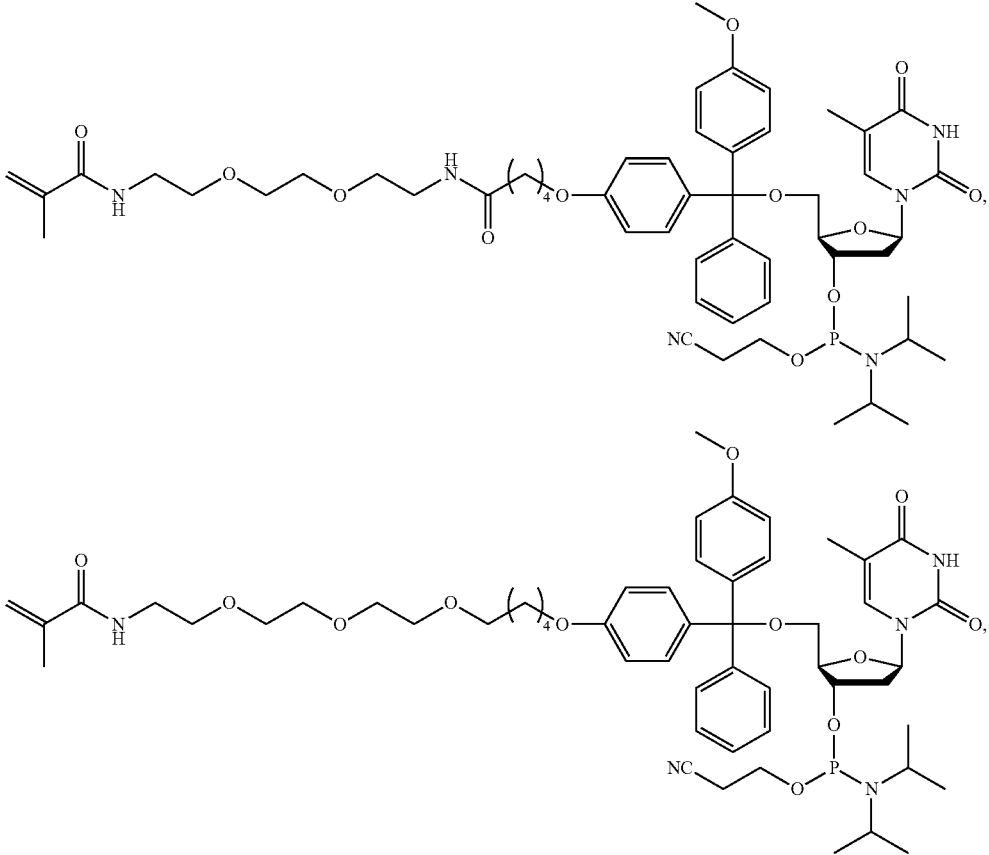

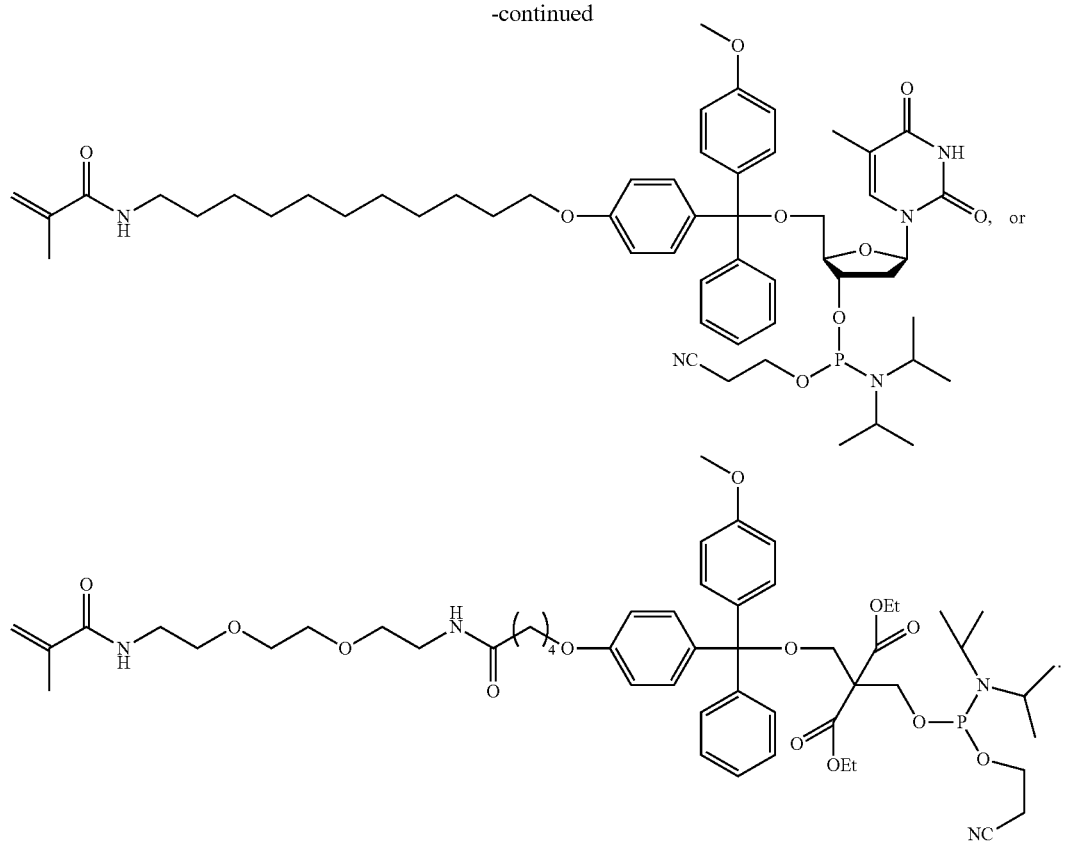
Suitable phosphoramidites also include compounds of formula (IIf):
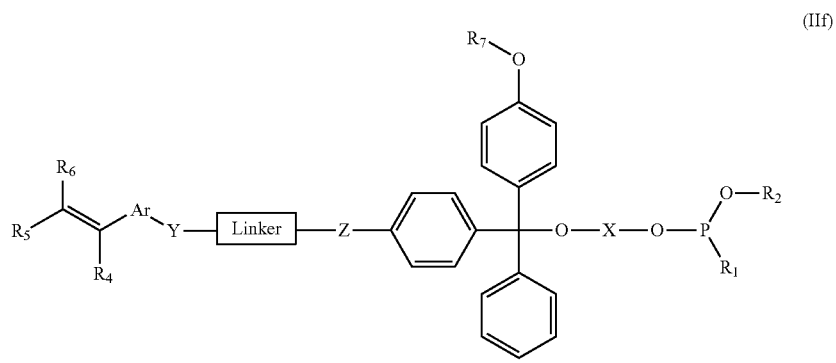
wherein:
X is selected from:
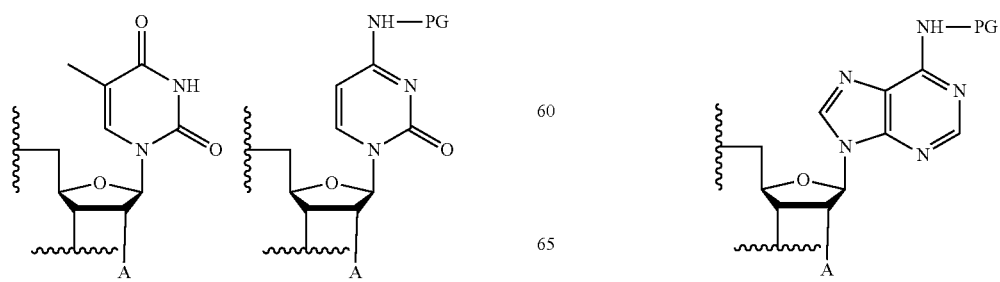

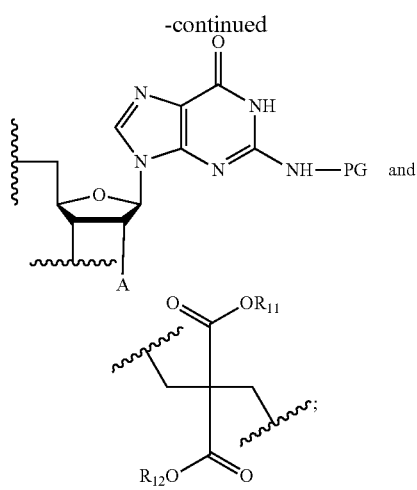

$R_1$ is halo or —$NR_aR_b$;
$R_2$ is —$CH_3$ or —$CH_2$—$CH_2$-EWG;
EWG is an electron-withdrawing group;
$R_{3b}$, $R_4$, $R_5$ and $R_6$ are each independently hydrogen or alkyl;
$R_7$, $R_8$, $R_9$, $R_{10}$, $R_{11}$, $R_{12}$, $R_{13}$, $R_a$ and $R_b$ are each independently alkyl;
Ar is arylenyl;
each A is independently selected from hydrogen and —O-PG;
each PG is independently selected from hydrogen and a protecting group;
each Z and Y are independently selected from —O—, —$CH_2$—, —S—, —C(=O)N($R_{13}$)—; —N($R_{13}$)C(=O)— or —N($R_{13}$)—;
linker is $(CH_2)_r$ or $(CH_2)_x[(CH_2)_xO(CH_2)_x]_p(CH_2)_y$ or $(CH_2)_x[(CH_2)_xO(CH_2)_x]_n(CH_2)_xN(R')C(=O)(CH_2)_m$ or $(CH_2)_rN(R')C(=O)(CH_2)_m$ or;
each x and y are independently an integer from 1 to 12;
r is an integer from 1 to 36;
p is an integer from 1 to 18; and
m is an integer from 1 to 18.

Suitable phosphoramidites include compounds of formula (IIg):

(IIg)

wherein:
X is selected from:

$R_1$ is halo or —$NR_aR_b$;
$R_2$ is —$CH_3$ or —$CH_2$—$CH_2$-EWG;
EWG is an electron-withdrawing group;
$R_{3a}$, $R_{3b}$, $R_4$, $R_5$ and $R_6$ are each independently hydrogen or alkyl;
$R_7$, $R_8$, $R_9$, $R_{10}$, $R_{11}$, $R_{12}$, $R_a$ and $R_b$ are each independently alkyl;
each A is independently selected from hydrogen and —O-PG;
each PG is independently selected from hydrogen and a protecting group;
u is an integer from 0 to 34; and
r is an integer from 1 to 36.

An exemplary capping agent of formula (IIg) is the following:

Suitable phosphoramidites also include compounds of formula (IIh):

(IIh)

wherein:
X is selected from:

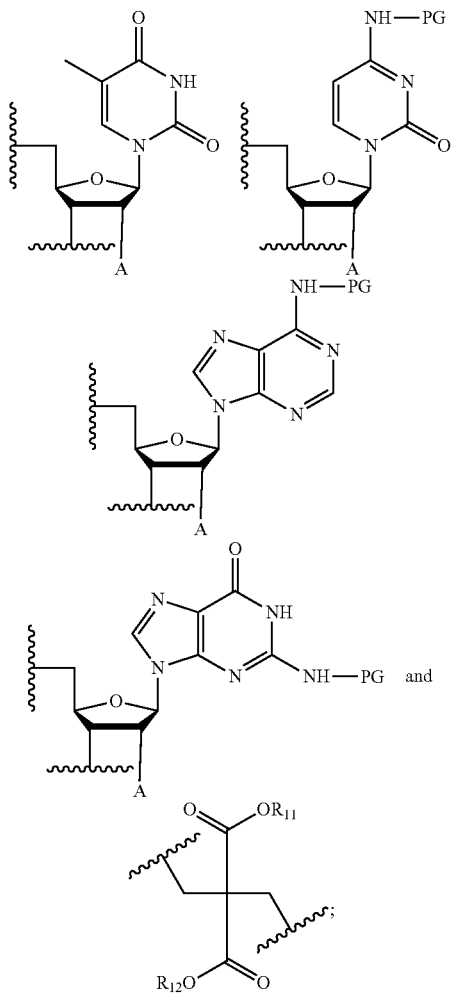

$R_1$ is halo or —$NR_aR_b$;
$R_2$ is —$CH_3$ or —$CH_2$—$CH_2$-EWG;
EWG is an electron-withdrawing group;
$R_{3b}$, $R_4$, $R_5$ and $R_6$ are each independently hydrogen or alkyl;
$R_7$, $R_8$, $R_9$, $R_{10}$, $R_{11}$, $R_{12}$, $R_{13}$, $R_a$ and $R_b$ are each independently alkyl;
Ar is arylenyl;
each A is independently selected from hydrogen and —O-PG;
each PG is independently selected from hydrogen and a protecting group;
Y is —O—, —$CH_2$—, —S—, —C(=O)N($R_{13}$)—; —N($R_{13}$)C(=O)— or —N($R_{13}$)—;
u is an integer from 0 to 34; and
w is an integer from 0 to 36.

When a compound of formula (IIa)-(IIh) is used for purification of oligonucleotides by polymerization, the full-length oligonucleotides can be released from the polymer using a fluoride-containing reagent such as HF or tetrabutylammonium fluoride.

Kits for Purifying Oligonucleotides

A further embodiment of the present invention is a kit comprising either a capping agent having a polymerizable functional group or a compound having a polymerizable functional group for attaching to the end of the full length oligonucleotide. Kits can further comprise monomers, coupling reagents, polymerization reagents, buffers, cleavage agents, and other components necessary to synthesize and purify an oligonucleotide in accordance with the present invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. All publications, patents and patent applications referenced in this specification are indicative of the level of ordinary skill in the art to which this invention pertains. All publications, patents and patent applications are herein expressly incorporated by reference to the same extent as if each individual publication or patent application was specifically and individually indicated by reference. In case of conflict between the present disclosure and the incorporated patents, publications and references, the present disclosure should control.

It also is specifically understood that any numerical range recited herein includes all values from the lower value to the upper value, i.e., all possible combinations of numerical values between the lowest value and the highest value enumerated are to be considered to be expressly stated in this application. For example, if a concentration range is stated as 1% to 50%, it is intended that values such as 2% to 40%, 10% to 30%, or 1% to 3%, etc., are expressly enumerated in this specification.

The following examples are provided to assist in a further understanding of the invention. The particular materials, methods and conditions employed are intended to be illustrative of the invention and are not limiting upon the scope of the invention.

EXAMPLES

General Experimental

All reactions were performed in oven-dried glassware either under a nitrogen atmosphere using standard Schlenk techniques or open to air through a Drierite tube. Reagents and solvents available from commercial sources were used as received unless otherwise noted. THF was distilled from Na/benzophenone ketyl. $CH_2Cl_2$ was distilled over $CaH_2$. Thin layer chromatography (TLC) was performed using Sigma-Aldrich TLC plates, silica gel 60F-254 over glass support, 0.25 µm thickness. Flash column chromatography was performed using Selecto Scientific silica gel, particle size 32-63 µm. Melting points were determined using a MEL-TEMP® melting point apparatus and were uncorrected. $^1$H, $^{13}$C and $^{31}$P NMR spectra were measured on a Varian UNITY INOVA spectrometer at 400, 100 and 162 MHz, respectively; chemical shifts (δ) were reported in reference to solvent peaks (residue $CHCl_3$ at δ 7.24 ppm for $^1$H and $CDCl_3$ at δ 77.00 ppm for $^{13}$C; residue $CHD_2OD$ at δ 3.31 ppm for $^1$H and $CD_3OD$ at δ 49.00 ppm for $^{13}$C) and $H_3PO_4$ (at δ 0.00 ppm for $^{31}$P). High-resolution mass spectra (HRMS) were obtained on a Finnigan Mat 95XL spectrometer. MALDI-TOF mass spectra were obtained on a Shimadzu Biotech Axima CFR-plus spectrometer. Oligonucleotides were synthesized on an ABI 394 solid phase synthesizer. HPLC was performed on a JASCO LC-2000Plus System: pump, PU-2089Plus Quaternary Gradient; detector UV-2075Plus. A C-18 reverse phase analytical column (5 µm diameter, 100 Å, 250×3.20 mm) was used. Solvent A: 0.1 M triethylammonium acetate, 5% acetonitrile. Solvent B: 90% acetonitrile. All profiles were generated by detection of absorbance of ON at 260 nm using the linear gradient solvent system: solvent B (0-45%) in solvent A over 60 minutes at a flow rate of 0.5 mL/minute. Aqueous NH$_4$OH (~29%), HF-pyridine (HF, ~70%; pyridine, ~30%) and Me$_3$SiOMe were purchased from Aldrich Inc. THF/pyridine/Pac$_2$O, succinic ester linked DMTr-dT-lcaa-CPG (pore size 1000 Å) and 5'-DMTr, 2-cyanoethyl phosphoramidites acetyl-dC, Pac-dA, 4-isopropyl-Pac-dG and dT were purchased from Glen Research, Inc. D-Salt™ dextran desalting column (5K MWCO) was purchased from Pierce Biotechnology, Inc.

Example 1

Synthesis of Capping Agent 1

Figure 4:
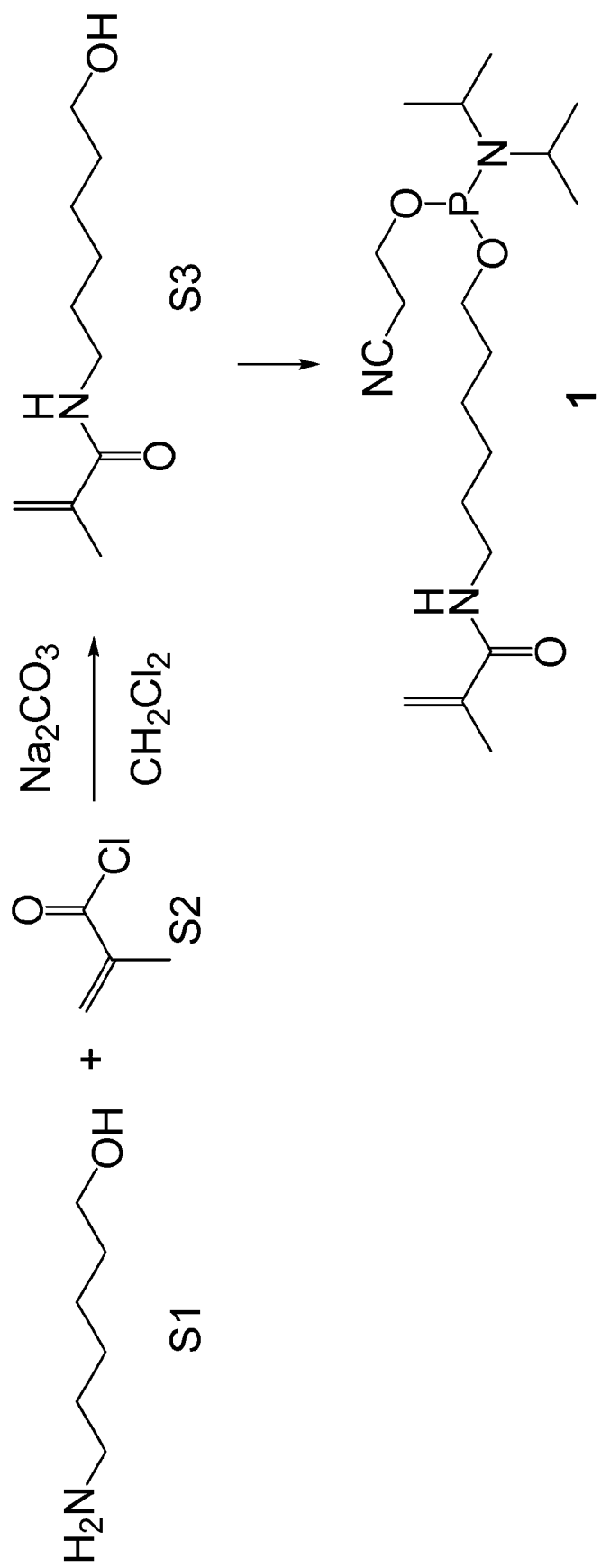
FIG. 4 represents the chemical reaction for synthesis of capping agent 1.

The synthesis of capping agent 1 is illustrated in FIG. 4.

Compound 1 was prepared as described in Zhu et al. *Angew. Chem. Int. Ed.*, 2010, 49, 1052-1056, though a different method was used to prepare S3. Compound S1 (5.0 g, 42.7 mmol), saturated Na$_2$CO$_3$ solution (50 mL) and CH$_2$Cl$_2$ (150 mL) were charged into a round bottom flask, and cooled to 0° C. To the solution was added the solution of S2 (4.46 g, 42.7 mmol) in CH$_2$Cl$_2$ (50 mL) dropwise with efficient stirring via an addition funnel. After addition, the mixture was stirred at room temperature for 3 hours, and then transferred into a separation funnel. The organic layer was separated. The aqueous phase was extracted with CH$_2$Cl$_2$ for three times. The combined organic phase was dried over anhydrous Na$_2$SO$_4$, and filtered. The solution was concentrated to give a sticky liquid (not completely dry). Ether was added until white solids appeared, which was re-dissolved by adding CH$_2$Cl$_2$. To make the solution more dilute, hexane and more CH$_2$Cl$_2$ were added. The solution was then put in a freezer (−20° C.) for 12 hours. Compound S3 was obtained as a colorless crystal: 7.33 g, 93% yield. If the compound melts at rt, a second crystallization from CH$_2$Cl$_2$/hexane may be desirable.

Example 2

Figure 5:
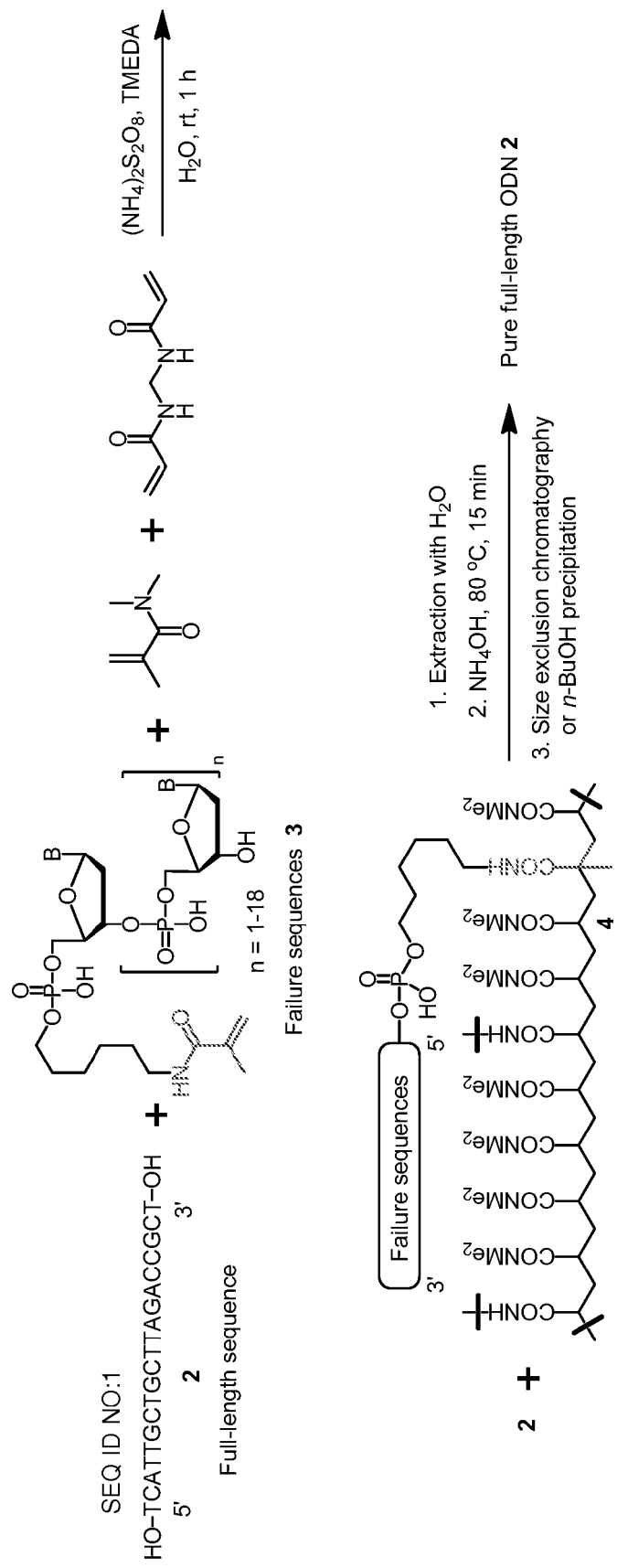
FIG. 5 illustrates an exemplary method of the invention, used to purify an exemplary oligodeoxynucleotide 2.
Figure 6:
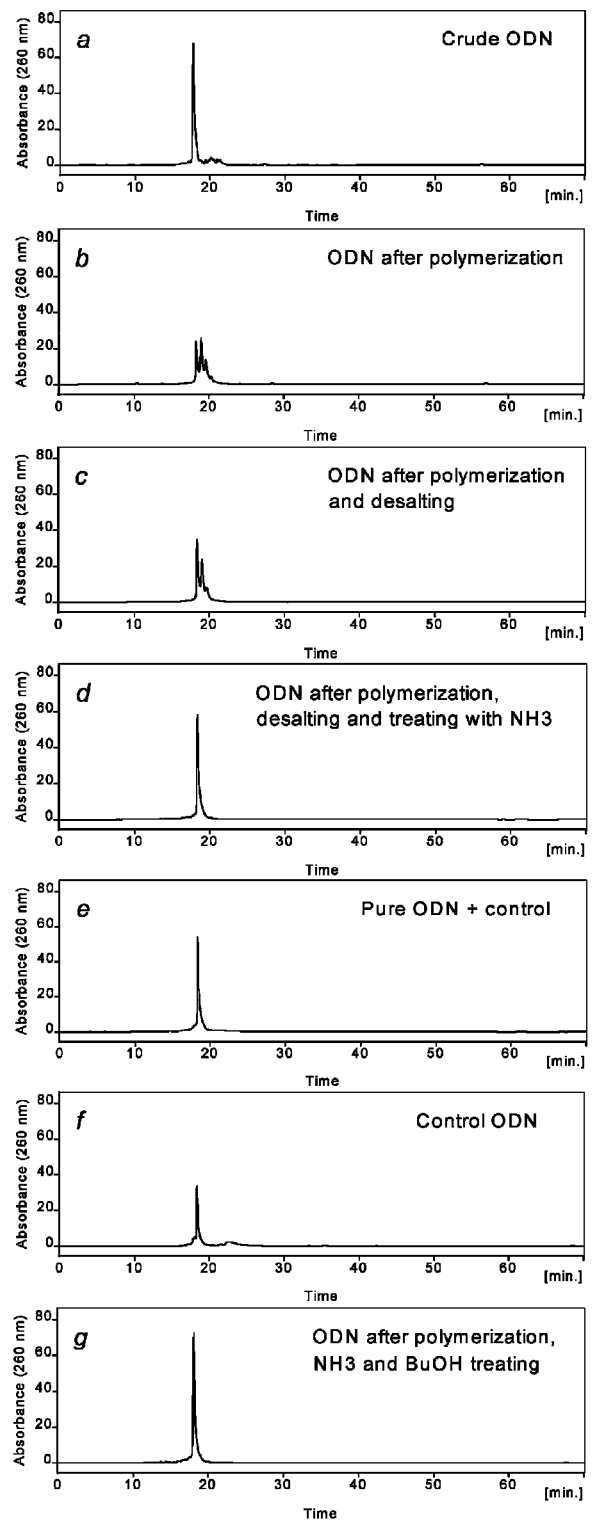
FIG. 6 depicts reverse-phase HPLC traces of oligodeoxynucleotide samples from the exemplary purification method illustrated in FIG. 5. (a) crude; (b) after polymerization; (c) after size exclusion chromatography; (d) after treating with NH$_4$OH; (e) co-injection with authentic sample; (f) control; (g) purified by polymerization and n-BuOH precipitation.

Synthesis of ODN 2 and its Purification by Polymerization of Failure Sequences The synthesis of ODN 2 is illustrated in FIG. 5. HPLC traces of various stages of the purification are illustrated in FIG. 6.

Synthesis of ODN 2.

ODN 2 was synthesized on a standard ABI 394 solid phase synthesizer using standard phosphoramidite chemistry under UltraMild conditions on controlled pore glass (CPG, pore size 1000 Å) on a 0.2 μmol scale. The succinyl ester linkage was used to anchor the ODN to CPG. The phosphoramidite monomers used were Pac-dA-CE, Ac-dC-CE, i-Pr-Pac-dG-CE and dT-CE. A 0.2 M solution of the polymerizable capping phosphoramidite 1 in acetonitrile was placed on the 5$^{th}$ bottle position, which is normally used for incorporating an additional base into ODN. The two bottles normally used to supply Ac$_2$O capping reagents were empty. In this synthesis, the capping failure sequences step was achieved using the polymerizable phosphoramidite 1 with 1H-tetrazole as the activator. The activator was from the same bottle that provided 1H-tetrazole for the coupling steps. To ensure complete capping, 1 and tetrazole were delivered to the synthesis column four times instead of two times normally used for standard nucleobase coupling. Between each delivery, a waiting time of 15 seconds was applied. The oxidation of the phosphite triesters between the capping agent and failure sequences was carried out for three times. In the last synthetic cycle, the DMTr group was removed. Cleavage and deprotection were carried out on the synthesizer with concentrated NH$_4$OH (900 min×4) at room temperature. The ODN solution was distributed equally into 4 Eppendorf tubes (1.5 mL), and dried in a SpeedVac, separately (each portion contained ~50 nmol ODN, P$_1$-P$_4$). P$_1$ was dissolved in 150 μL water, 20 μL (~6.67 nmol) was injected into RP HPLC to generate trace a (FIG. 6). The full-length sequence appeared at ~19 minutes. The failure sequences were at ~20 minutes. The small peaks at around 10, 28, and 56 minutes were probably due to the small molecules from protecting groups. The very small peaks, which could be hardly seen in a at the left of the full-length sequence, might be resulted from un-capped failure sequences, deletion sequences, or damaged sequences.

Polymerization of Failure Sequences.

The remaining 130 μL solution of P$_1$ was transferred into a 2-necked round bottom flask. The Eppendorf tube was washed with water (50 μL×3); the washes were also placed into the same flask. To the flask was added the pre-formed polymerization solution [250 μL; dimethylacrylamide 1.69 M, N,N'-methylenebis(acrylamide) 16.9 mM; the solution could be stored at −20° C. in dark for 1 month]. The flask was flushed with nitrogen for 2 minutes with gentle stirring. (NH$_4$)$_2$S$_2$O$_8$ (10%, 5 μL) and N,N,N',N'-tetramethylethylenediamine (TMEDA, 5 μL) were added sequentially via pipettes under positive nitrogen pressure. The solution was stirred gently under nitrogen at room temperature. A gel, which was the ODN failure sequences-polyacrylamide conjugate, was formed within 30 minutes. The gel was allowed to stand for another 30 minutes to ensure completion of polymerization.

Extraction of Full-Length Sequence.

To the gel, which was broken into several pieces, was added water (200 μL). The mixture was stirred gently at room temperature for 3 hours. The supernatant was transferred into an Eppendorf tube. The gel was further extracted with water for 2 times (200 μL, rt, 12 h; 200 μL, rt, 3). The supernatants were combined and evaporated into dryness. The ODN was dissolved into 130 μL water; 20 μL was injected into HPLC to generate trace b (FIG. 6). As shown, the failure sequences were removed, but the full-length sequence appeared as 4 peaks. The small peaks resulted from small molecules from protecting groups also remained as expected.

Size Exclusion Chromatography to Remove Small Molecules.

A 10 mL D-Salt™ dextran desalting column (5K MWCO) was used. The column was first washed with water (20 mL). The remaining 110 μL solution of ODN 2 was loaded to the top of the column. The Eppendorf tube was washed with water (100 μL×3), and the washes were also loaded to the column. The column was washed with 1.59 mL water. This first 2 mL eluent did not contain any ODN. The elution was continued and the next 5 mL was collected and evaporated to dryness. The residue was dissolved in 110 μL water, 20 μL was injected into HPLC to generate trace c (FIG. 6). As shown, the small molecules from protecting groups were removed. The 4 peaks at around 19 minutes were merged into 3. The desalting column was recovered by washing with water (20 mL), and was stored in 0.02% NaN$_3$ solution.

Treating with Concentrated NH$_4$OH.

The remaining 90 μL solution of ODN 2 was evaporated to dryness in an Eppendorf tube. Concentrated NH$_4$OH (300 μL) was added. The solution was heated to 80° C. for 15 minutes in a sand bath. After evaporation to dryness, the residue was dissolved into 90 μL water, 20 μL was injected into HPLC to generate trace d (FIG. 6). As shown, only one peak is observed, and the ODN is pure. The recovery yield of the purification process (polymerization, extraction, size exclusion chromatography and NH$_4$OH treatment) was estimated to be 83% by comparing the area of the peak in trace d with that in trace a at ~19 min (FIG. 6).

Identification of ODN 2.

The authentic ODN of 2 was synthesized using standard phosphoramidite chemistry on a 1 μmol scale and purified with trityl-on RP HPLC at The Midland Certified Reagent Company, Inc. (Midland, Tex., USA). MALDI-TOF spectrum of the authentic ODN was also obtained at the company showing correct molecular weight: calcd for [M−H]⁻ 6057. found 6060. At Michigan Tech, the authentic sample was divided equally into portions (each portion contains ~100 nmol ODN assuming the yield for the synthesis and purification was 100%). One portion was dissolved in 150 μL water, 20 μL was injected into RP HPLC to generate trace f (FIG. 6). To compare ODN 2 synthesized in our lab and purified using our catching failure sequences by polymerization technique with the authentic sample, 10 μL of the solution used to generate trace d and 10 μL of the solution used to generate trace f were mixed, and injected into RP HPLC to generate trace e (FIG. 6). A single peak was observed showing the two were identical. ODN 2 was also characterized with MALDI-TOF: calcd for [M−H]⁻ 6057. found: 6057. The spectrum is attached in the "MALDI-TOF mass spectrum of ODN 2 purified by polymerization of failure sequences approach" section of these Examples.

ODN Purification by Polymerization of Failure Sequences and n-BuOH Precipitation.

The ODN 2 (P$_2$, ~50 nmol) was dissolved into 150 μL water, 20 μL was injected into HPLC, which gave a trace exactly the same as a (FIG. 6). The remaining 130 μL ODN solution was subjected into the procedure of polymerization of failure sequences and extraction of full-length sequence as described above. The size exclusion chromatography step was not performed. To the full-length sequence, which contained 4 ODNs and small organic molecules from protecting groups, was added concentrated NH$_4$OH (100 μL). The solution was vortexed shortly and then heated to 80° C. for 30 minutes. This converted the modified ODNs to the un-modified one. After cooling to room temperature, n-BuOH (1 mL) was added. The mixture was vortexed for 30 seconds and then centrifuged at 14.5K for 5 minutes. The supernatant was removed. The residue was re-dissolved into 50 μL water, 500 μL n-BuOH was added. Vortexed and centrifuged again, and the supernatant was removed. This removed the small organic molecules resulted from deprotection. The ODN was dissolved in 130 μL water, 20 μL was injected into HPLC to generate trace g (FIG. 6). As shown, the ODN is pure. The recovery yield of the procedure (polymerization, extraction, NH$_4$OH treatment and n-BuOH precipitation) was estimated to be more than 85% by comparing the area of the peak in trace g with that in trace a at ~19 min.

Example 3

Synthesis of Capping Agent 5

Figure 7:
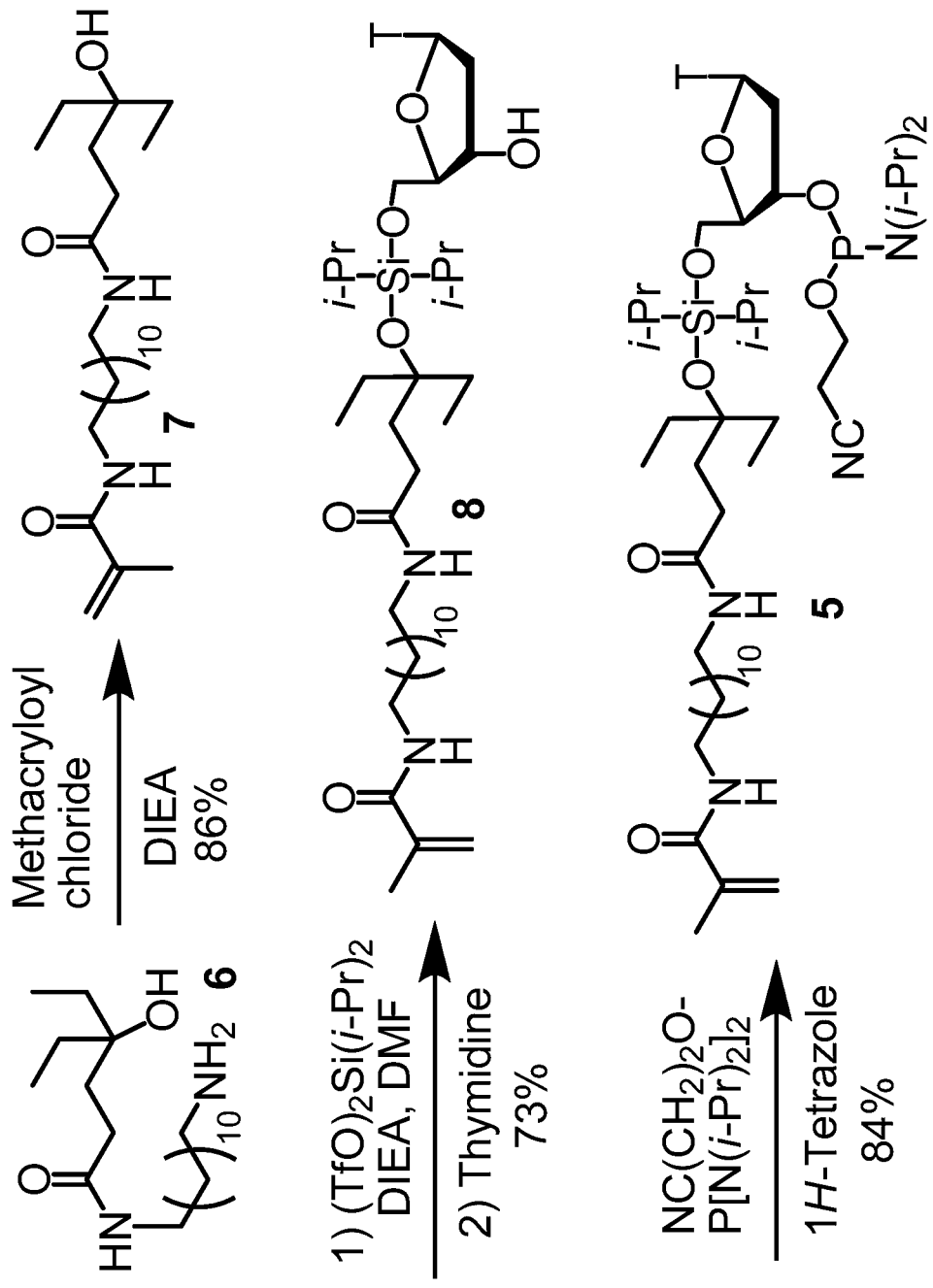
FIG. 7 represents the chemical reaction for synthesis of capping agent 5.

The synthesis of compound 5 is illustrated in FIG. 7.

γ,γ-Diethyl-γ-Butyrolactone

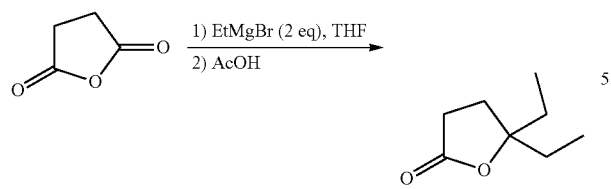

Succinic anhydride (15.0 g, 150 mmol, 1.0 eq) was added into a round bottomed flask, and the flask was flushed with nitrogen. THF (500 mL) was then added via a syringe. The solution was cooled to 0° C. Methyl magnesium bromide in ether (3.0 M, 100 mL, 300 mmol, 2.0 eq) was added via syringe slowly. The reaction mixture was warmed to room temperature gradually, and then heated to 50° C. for 12 hours. A yellow solution was formed. After cooling the reaction mixture to room temperature, AcOH was added until pH=4, and stirring was continued for an additional 12 hours. Water (75 mL) was added, and THF and ether were removed under reduced pressure. The green suspension was extracted with CH$_2$Cl$_2$ (60 mL×5), and the organic phase was dried over anhydrous Na$_2$SO$_4$ and concentrated. Purification by vacuum distillation gave the product as brown oil (9.7 g, 46%). This compound has been synthesized using several different methods in the literature.

N-(12-Aminododecyl)-4-hydroxy-4-ethyl-hexanamide (6)

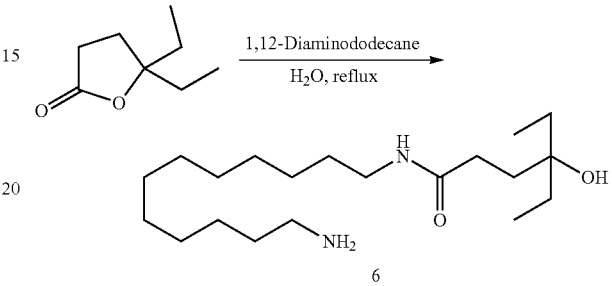

A procedure reported previously by us was followed. γ,γ-Diethyl-γ-butyrolactone (2.7 g, 19.1 mmol, 1.0 eq), 1,12-diaminododecane (9.6 g, 47.7 mmol, 2.5 eq), and water (8.0 mL) were combined. The solution was refluxed under a nitrogen atmosphere overnight. A yellow solution was formed. After cooling to room temperature, water was removed under reduced pressure. The yellow oily residue was purified by flash column chromatography (SiO$_2$, Et$_2$O/CH$_3$OH/CH$_3$CN/Et$_3$N=5:2:2:1) to give 6 as a light yellow solid (2.0 g, 30%): R$_f$=0.5 (SiO$_2$, Et$_2$O/CH$_3$OH/CH$_3$CN/Et$_3$N=5:2:2:1); $^1$H NMR (400 MHz, CDCl$_3$) δ 5.67 (br s, 1H), 3.20 (q, 4H, J=7.2 Hz), 2.67 (t, 2H, J=7.2 Hz), 2.25 (t, 2H, J=7.2 Hz), 2.02 (br s, 3H), 1.74 (t, 2H, J=7.2 Hz), 1.50-1.40 (m, 8H), 1.33-1.20 (m, 16H), 0.84 (t, 6H, J=7.6 Hz); $^{13}$C NMR (100 MHz, CDCl$_3$) δ 174.2, 73.9, 42.2, 39.9, 33.7, 31.0, 30.9, 29.73, 29.69, 29.4, 27.1, 27.0, 8.1; HRMS (ESI) m/z calcd for C$_{20}$H$_{43}$N$_2$O$_2$ [M+H]⁺ 343.3325. found 343.3321.

Methacrolyl Tertiary Alcohol (7)

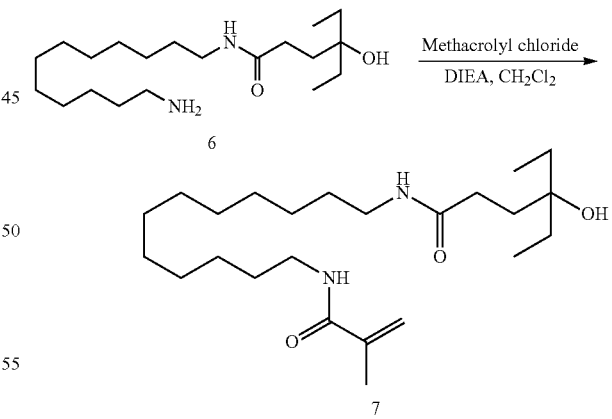

To a round bottomed flask under a nitrogen atmosphere was added diisopropylethylamine (750 μL, 4.31 mmol, 2.5 eq), 6 (0.6 g, 1.75 mmol, 1.0 eq), and CH$_2$Cl$_2$ (120 mL). The solution was cooled to 0° C. Methacrolyl chloride (171 μL, 1.75 mmol, 1.0 eq) was added via a syringe. The flask was then detached from the nitrogen atmosphere and connected to air via a Drierite tube. The reaction mixture was stirred at room temperature overnight. The contents were then transferred into a separation funnel, and were washed with water (50 mL), which was extracted with CH$_2$Cl$_2$ (50 mL×2). The combined organic phase was dried over anhydrous $Na_2SO_4$. Volatiles were then removed under reduced pressure. The crude product was purified by flash column chromatography ($SiO_2$, $CH_2Cl_2/CH_3OH$=97:3) giving pure 7 as a white solid (0.6 g, 86%): $R_f$=0.7 ($SiO_2$, $CH_2Cl_2/CH_3OH$=9:1); $^1H$ NMR (400 MHz, $CDCl_3$) δ 5.85 (br s, 2H), 5.63-5.62 (m, 1H), 5.28-5.27 (m, 1H), 3.26 (dt, 2H, J=8.4, 6.0 Hz), 3.18 (dt, 2H, J=6.8, 6.0 Hz), 2.52 (br s, 1H), 2.25 (t, 2H, J=7.2 Hz), 1.93 (dd, 3H, J=1.2, 0.8 Hz), 1.73 (t, 2H, J=7.2 Hz), 1.52-1.41 (m, 8H), 1.31-1.20 (m, 16H), 0.83 (t, 6H, J=7.6 Hz); $^{13}C$ NMR (100 MHz, $CDCl_3$) δ 174.2, 168.6, 140.5, 119.3, 73.9, 39.9, 33.6, 31.1, 30.9, 29.7, 29.6, 29.4, 27.1, 18.9, 8.1; HRMS (ESI) m/z calcd for $C_{24}H_{47}N_2O_3$ $[M+H]^+$ 411.3587. found 411.3582.

Methacrolyl Thymidine (8)

thymidine (162 mg, 1.0 mmol, 1 eq) in dry DMF (1.5 mL) was added via a cannula. After stirring at 0° C. for 3 hours, DMF was removed under vacuum. To the residue, ice-cooled EtOAc (60 mL) and $NaHCO_3$ solution (5%, 50 mL) were added, and the phases were separated. The aqueous phase was further extracted with ice-cooled EtOAc (50 mL×4). The organic phase was dried over anhydrous $Na_2SO_4$. EtOAc was removed under reduced pressure to give the crude product as a yellow oil, which was purified by flash column chromatography ($SiO_2$, $CH_2Cl_2/CH_3OH$=100:0 to 95:5) to give pure 8 as a white foam (370 mg, 73%): $R_f$=0.6 ($SiO_2$, $CH_2Cl_2/CH_3OH$=9:1); $^1H$ NMR (400 MHz, $CD_3OD$) δ 7.92 (br s, 1H), 7.82 (br t, 1H, J=5.2 Hz), 7.49 (s, 1H), 6.24 (dd, 1H, J=7.2, 3.2 Hz), 5.64 (s, 1H), 5.32 (s, 1H), 4.20 (dt, 1H, J=6.4, 2.8 Hz), 4.02-3.91 (m, 3H), 3.24-3.16 (m, 2H), 3.16-3.09 (m, 2H), 2.29-2.13 (m, 4H), 1.91 (dd, 3H, J=1.6, 0.8 Hz), 1.86 (d,

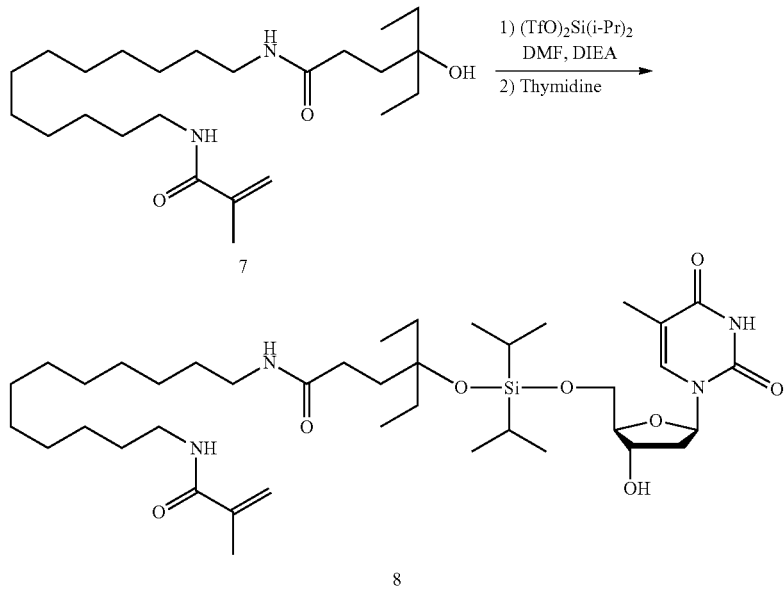

Compound 7 (274 mg, 1.0 mmol, 1 eq) in a 2-necked round bottomed flask was dried under vacuum. The flask was then refilled with nitrogen. The vacuum-nitrogen cycle was repeated for two additional times. Dry DMF (5 mL) and diisopropylethylamine (350 µL, 3.0 mmol, 3 eq) were then added via syringes. After cooling to 0° C., diisopropylsilyl bis(trifluoromethanesulfonate) (196 µL, 1.0 mmol, 1 eq) was added via a syringe in one portion. The solution was stirred at 0° C. for 1 hour and room temperature for 2 hours. The reaction mixture was then cooled to 0° C. again. A solution of 3H, J=1.2 Hz), 1.86-1.81 (m, 2H), 1.66-1.40 (m, 8H), 1.36-1.24 (m, 16H), 1.12-1.00 (m, 14H), 0.90 (t, 6H, J=7.2 Hz); $^{13}C$ NMR (100 MHz, $CD_3OD$) δ 174.6, 170.0, 165.0, 151.0, 140.3, 136.2, 118.9, 110.3, 87.3, 84.8, 79.0, 70.7, 62.9, 39.8, 39.5, 39.2, 34.7, 31.61, 31.57, 30.7, 29.5, 29.3, 26.9, 26.8, 17.7, 17.42, 17.36, 17.32, 17.29, 13.8, 13.7, 11.5, 7.7; HRMS (ESI) calcd for $C_{40}H_{73}N_4O_8Si$ $[M+H]^+$ 765.5198. found 765.5186.

Methacrolyl Thymidine Phosphoramidite (5)

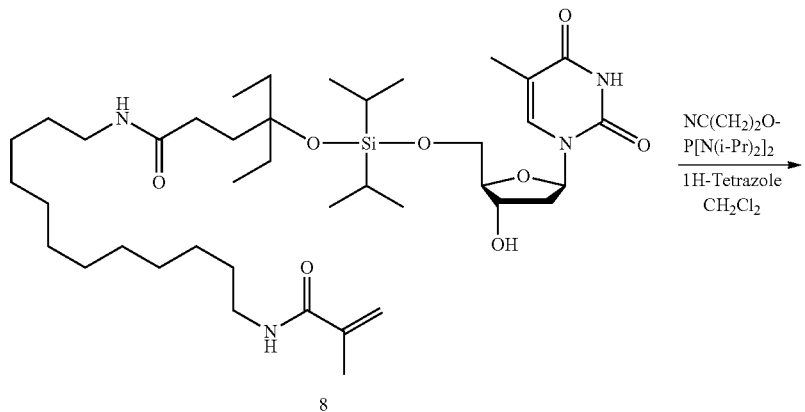

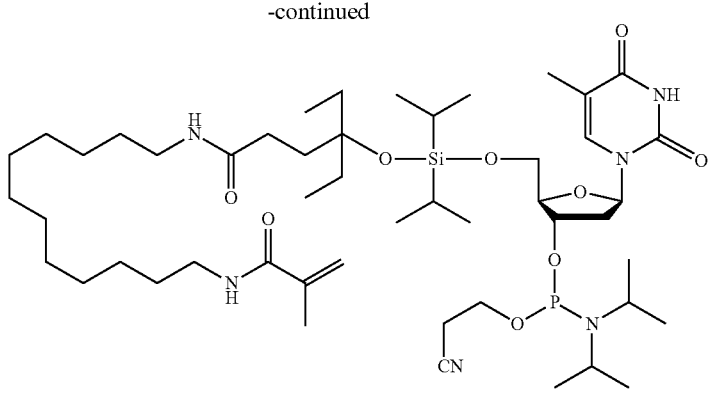

A round bottomed flask containing 8 (150 mg, 0.20 mmol, 1.0 eq) was flushed with nitrogen. Dry $CH_2Cl_2$ (6.0 mL) and 2-cyanoethyl-N,N,N',N'-tetraisopropylphosphoramidite (68 μL, 0.22 mmol, 1.1 eq) were added via syringes sequentially. To the resulting solution was added the solution of 1H-tetrazole in $CH_3CN$ (0.45 M, 480 μL, 0.22 mmol, 1.1 eq) in three portions over a period of 1 hour. After stirring at room temperature for another 2 hours, the reaction mixture was concentrated under reduced pressure. The residue was purified by flash column chromatography ($SiO_2$, hexanes/$CH_2Cl_2$/$Et_3N$=1:2:0.3) to give 5 as a white foam (158 mg, 84%): $R_f$=0.5 ($SiO_2$, hexanes/$CH_2Cl_2$/$Et_3N$=1:2:0.3); $^1H$ NMR (400 MHz, $CDCl_3$) δ 7.37 (s, 0.7H), 7.32 (s, 0.3H), 6.29 (dd, 1H, J=8.0, 6.4 Hz), 5.63 (s, 1H), 5.27 (q, 1H, J=1.2 Hz), 4.61-4.52 (m, 1H), 4.18-3.52 (m, 7H), 3.32-3.21 (m, 2H), 3.21-3.10 (m, 2H), 2.67-2.56 (m, 2H), 2.50-2.34 (m, 1H), 2.24-2.14 (m, 2H), 2.13-2.02 (m, 1H), 1.95-1.91 (m, 3H), 1.87 (s, 3H), 1.87-1.79 (m, 2H), 1.64-1.38 (m, 8H), 1.30-1.10 (m, 28H), 1.10-0.95 (m, 14H), 0.85 (t, 6H, J=7.2 Hz); $^{13}C$ NMR (100 MHz, $CDCl_3$) δ 173.1, 168.6, 163.8, 150.4, 140.5, 135.5, 119.2, 117.8, 111.2, 86.7, 86.3 (d, J=6.1 Hz), 84.8, 84.6, 79.3, 73.6 (d, J=18.3 Hz), 62.8, 58.3 (d, J=18.0 Hz), 43.5 (d, J=12.2 Hz), 39.9, 39.7, 34.7, 34.6, 32.0, 31.9, 31.2, 29.8, 29.75, 29.67, 29.46, 29.43, 27.1, 24.84, 24.77, 24.74, 24.6, 20.6, 18.9, 18.29, 18.26, 18.13, 18.06, 14.1, 14.0, 13.7, 12.5, 8.7; $^{31}P$ NMR (162 MHz, $CDCl_3$) δ 150.1, 149.8.

Example 4

Synthesis of Oligonucleotide 9

Figure 9:
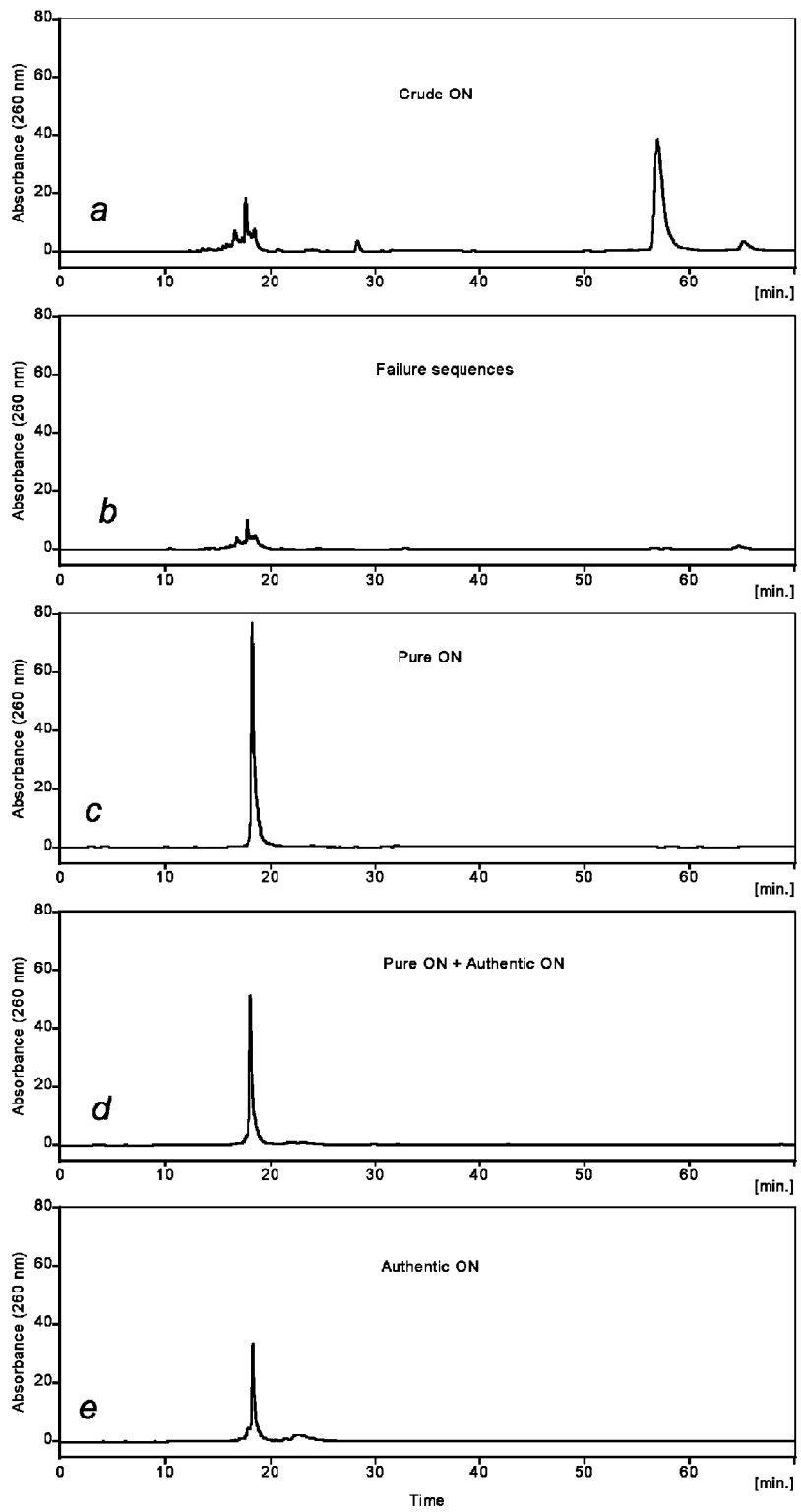
FIG. 9 depicts reverse-phase HPLC traces of oligodeoxynucleotide samples from the exemplary purification method illustrated in FIG. 8. (a) Crude oligodeoxynucleotide product containing full-length sequence 10, failure sequences 11 and other impurities; (b) Failure sequences 11 and other impurities that were removed from the gel after catching the full-length sequence 10 by polymerization; (c) Oligodeoxynucleotide 9 purified by catching by polymerization, washing and releasing; (d) Oligodeoxynucleotide 9 and an authentic sample purchased from a commercial source; (e) Authentic sample purchased from a commercial source.
Figure 10:
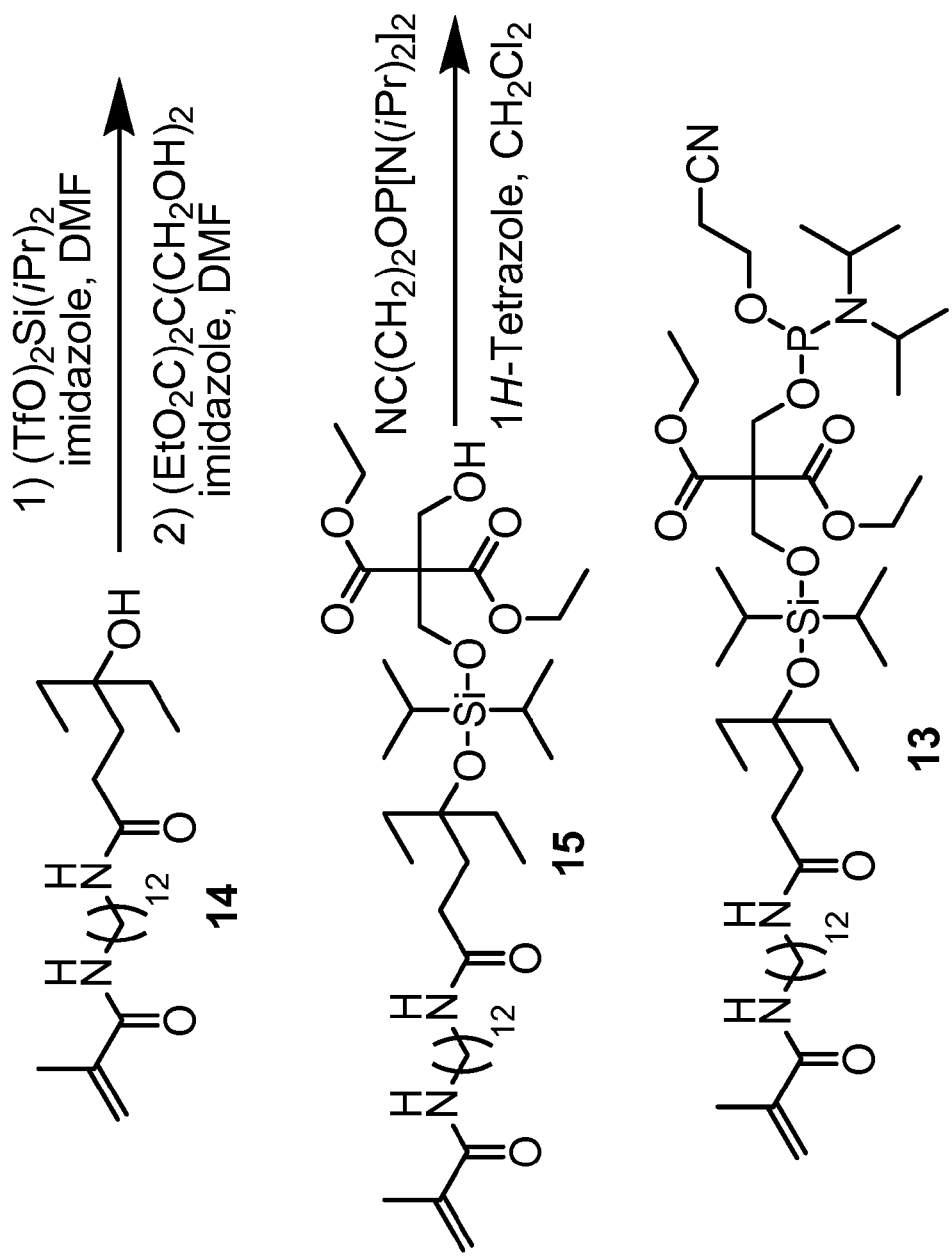
FIG. 10 represents the chemical reaction for synthesis of capping agent 13.

ON 9 was synthesized on an ABI 394 solid phase synthesizer using standard phosphoramidite chemistry under Ultra-Mild conditions on controlled pore glass (CPG, pore size 1000 Å) on a 1 μmol scale. The succinyl ester linkage was used to anchor the ON to CPG. The phosphoramidite monomers used were Pac-dA-CE, Ac-dC-CE, iPr-Pac-dG-CE and dT-CE. Manufacture recommended synthetic cycles were adopted. In the last synthetic cycle, phosphoramidite 5 (in acetonitrile, 0.1 M, which is two times of normal phosphoramidite concentration) was coupled to 5'-end of the ON for 5 minutes. Detritylation was not performed in the last synthetic cycle. Cleavage and deprotection were carried out on the synthesizer with concentrated $NH_4OH$ (900 minutes×4) at room temperature. The solution was distributed equally into 20 Eppendorf tubes (1.5 mL), and dried in a SpeedVac, separately (each portion contained ~50 nmol ON, $P_1$-$P_{20}$). $P_1$ was dissolved in 80 μL water, 20 μL (~12.5 nmol) was injected into RP HPLC to generate trace a (FIG. 9).

Example 5

Figure 8:
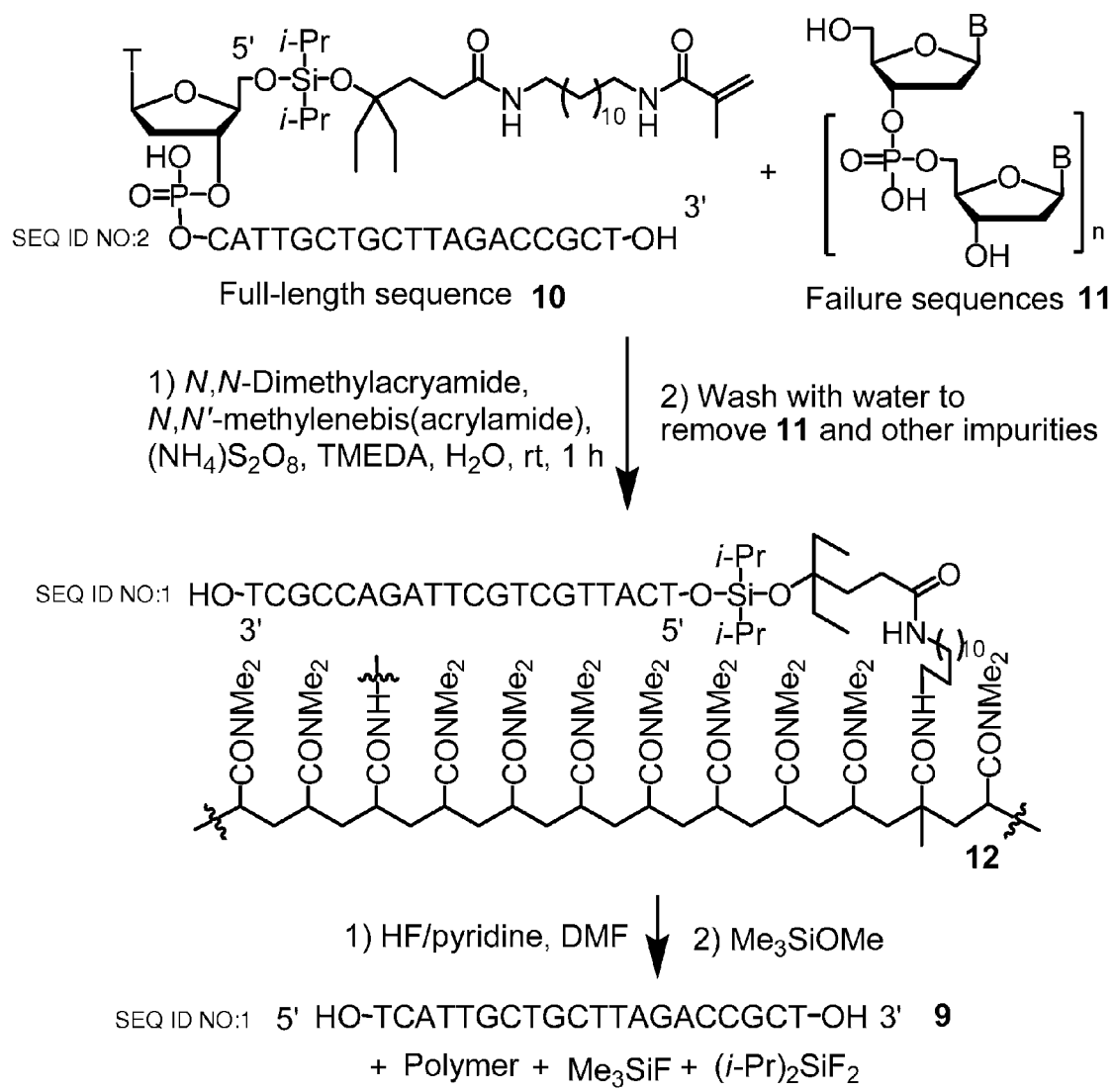
FIG. 8 illustrates an exemplary method of the invention, used to purify an exemplary oligodeoxynucleotide 9.

Purification Via Radical Acrylamide Polymerization of Full-Length Sequences The purification of oligonucleotide 9 is illustrated in FIG. 8. The crude ON 10 ($P_2$) was transferred into a 25 mL 2-necked round bottomed flask by dissolving into water (100 μL, 50 μL×3). To the flask was also added aqueous dimethylacrylamide solution (250 μL; dimethylacrylamide 1.69 M, N,N'-methylenebis(acrylamide) 16.9 mM; the solution could be stored at −20° C. in dark for 1 month). The flask was flushed with nitrogen for 2 minutes with gentle stirring. $(NH_4)_2S_2O_8$ (10%, 5 μL) and N,N,N',N'-tetramethylethylenediamine (TMEDA, 5 μL) were added sequentially via pipettes under positive nitrogen pressure. The solution was stirred gently under nitrogen at room temperature. A gel, which was the ON-polyacrylamide conjugate 12, was formed within 30 minutes. The gel was allowed to stand for another 30 minutes to ensure completion of polymerization.

Washing—Removal of Failure Sequences 11 and Other Impurities

The gel 12 in the 2-necked round bottomed flask was broken into smaller pieces with a glass rod. Water (5 mL) was added via a pipette. The content was gently stirred overnight at room temperature. The supernatant, which contains failure sequences 11 and other impurities, was removed using a pipette. To analyze the efficiency of the catching by polymerization process, the supernatant was concentrated to ~1 mL and desalted using a D-Salt™ dextran desalting column (5K MWCO). After concentration to dryness in a SpeedVac concentrator, 80 μL water was added, 20 μL was injected into RP HPLC to generate trace b (FIG. 9). The gel was further rinsed with water (3 mL/1 hour×3) to ensure complete removal of impurities.

Releasing—Cleavage of Full-Length ON 9 from Polymer

The gel 12 was transferred into a 1.5 mL Eppendorf tube and dried under vacuum overnight. To the tube was added dry DMF (1 mL) and HF-pyridine (30 μL), the tube was vortexed shortly, and then was allowed to stand for 5 hours at room temperature. At this stage, ON 9 was cleaved from the polymer. The supernatant was transferred into another Eppendorf tube. To the gel was added $Me_3SiOMe$ (300 μL). After standing at room temperature for 30 minutes, $Me_3SiOMe$ was combined with the supernatant, and mixture was allowed to stand at room temperature for a minimum of 15 minutes. The gel was transferred into a round bottomed flask. Water (5 mL) was added. The mixture was stirred gently at room temperature for 12 hours. The supernatant was removed using a pipette. The gel was further extracted with water (3 mL/2 hours×2). All supernatants (DMF, Me$_3$SiOMe and water) were combined and dried to dryness. The residue was dissolved in 80 µL water, 20 µL was injected into RP HPLC to generate trace c (FIG. 9). The recovery yield for the purification process was estimated to be 72% by comparing the area of the peak in trace c at 19 minutes with that in trace a at 57 minutes.

Identification of ON 9

The authentic ON of 9 was synthesized using standard phosphoramidite chemistry on a 1 µmol scale and purified with trityl-on RP HPLC at The Midland Certified Reagent Company, Inc. (Midland, Tex., USA). MALDI-TOF spectrum of the authentic ON was also obtained at the company showing correct molecular weight: calculated for [M−H]$^−$ 6058. found 6060. The authentic sample was divided equally into 20 portions (each portion contains ~50 nmol ON assuming the yield for the synthesis and purification was 100%). One portion was dissolved in 80 µL water, 20 µL was injected into RP HPLC to generate trace e (FIG. 9). To compare ON 9 synthesized in our lab and purified using our catching by polymerization, washing and releasing technique with the authentic sample, 10 µL of the solution used to generate trace c and 10 µL of the solution used to generate trace e were mixed, and injected into RP HPLC to generate trace d (FIG. 9). A single peak was observed showing the two were identical. ON 9 was also characterized with MALDI-TOF: calcd for [M−H]$^−$ 6058. found: 6057.

Example 6

Synthesis of Compound 13

Synthesis of Compound 15

A round-bottomed flask containing compound 14 (200 mg, 0.49 mmol, 1.0 equiv) and a magnetic stirring bar was evacuated and then refilled with nitrogen. The evacuation and nitrogen-filling cycle was repeated for two more times. Dry DMF (2 mL) and diisopropylethylamine (254 µL, 1.46 mmol, 3.0 equiv) were added via a syringe. The mixture was cooled to 0° C. Diisopropylsilyl bis(trifluoromethanesulfonate) (144 µL, 0.487 mmol, 1.0 equiv) in dry DMF (1 mL) was added via a syringe in one portion at 0° C. The solution was stirred at 0° C. for 1 hour and room temperature for 2 hours. Imidazole (50 mg, 0.73 mmol, 1.5 equiv) in dry DMF (1 mL) was added via a syringe. The solution was stirred for 1 hour, and then added to a flask containing diethyl bis(hydroxymethyl)malonate (107 mg, 0.487 mmol, 1.0 equiv), imidazole (33 mg, 0.487 mmol, 1 equiv) and DMF (2 mL) at 0° C. via a cannula slowly. The reaction mixture was stirred at 0° C. for 4 hours, and then quenched with 5% NaHCO$_3$ (0° C., 50 mL). EtOAc (0° C., 30 mL) was added, and the phases were separated. The aqueous phase was extracted with EtOAc (0° C., 30 mL×3). The combined organic phase was dried over anhydrous Na$_2$SO$_4$ and filtered. The filtrate was evaporated under reduced pressure to give a yellow oil. Purification with flash column chromatography (SiO$_2$, hexanes/EtOAc, 3:1 to 1:1) gave 15 as a pale yellow oil (151 mg, 42%): R$_f$=0.60 (SiO$_2$, hexanes/EtOAc, 1:2); $^1$H NMR (400 MHz, CDCl$_3$) δ 6.07 (br s, 1H), 5.94 (br s, 1H), 5.614-5.609 (m, 1H), 5.25-5.24 (m, 1H), 4.23 (s, 2H), 4.21-4.08 (m, 6H), 3.86 (br s, 1H) 3.26-3.21 (m, 2H), 3.18-3.13 (m, 2H), 2.26-2.14 (m, 2H), 1.91-1.90 (m, 3H), 1.83-1.77 (m, 2H), 1.53-1.37 (m, 8H), 1.25-1.19 (m, 22H), 0.99-0.95 (m, 14H), 0.83-0.76 (m, 6H); $^{13}$C NMR (100 MHz, CDCl$_3$) δ 173.8, 169.3, 168.7, 140.4, 119.3, 78.8, 61.8, 61.6, 61.5, 61.4, 39.9, 39.8, 34.7, 31.6, 31.3, 31.1, 30.9, 29.7, 29.6, 29.4, 27.1, 18.9, 18.1, 17.9, 14.4, 14.2, 13.7, 8.5; HRMS (ESI, [M+Na]$^+$) calcd for C$_{39}$H$_{74}$N$_2$NaO$_9$Si 765.5061. found 765.5069.

Synthesis of Phosphoramidite 13

A round-bottomed flask containing 15 (119 mg, 0.16 mmol, 1.0 equiv) and a magnetic stirring bar was evacuated and then refilled with nitrogen. The evacuation and nitrogen-filling cycle was repeated for two more times. Dry CH$_2$Cl$_2$ (5 mL) and 2-cyanoethyl-N,N,N',N'-tetraisopropylphosphoramidite (60 µL, 0.176 mmol, 1.1 equiv) were then added via syringe. A 1H-tetrazole solution in CH$_3$CN (0.45 M, 391 µL, 0.176 mmol, 1.1 equiv) was added via syringe in one portion. After stirring at room temperature for 2 hours, the reaction mixture was concentrated to dryness under reduced pressure. The residue was purified with flash column chromatography (SiO$_2$, hexanes/EtOAc/Et$_3$N=3:1:1) giving 13 as a colorless oil (150 mg, 99%): R$_f$=0.40 (SiO$_2$, hexanes/EtOAc/Et$_3$N=3:1:1); $^1$H NMR (400 MHz, CDCl$_3$) δ 6.00 (br s, 1H), 5.85 (br s, 1H), 5.64-5.60 (m, 1H), 5.263-5.257 (m, 1H), 4.23-4.10 (m, 8H), 3.80-3.71 (m, 2H), 3.56-3.47 (m, 2H), 3.28-3.23 (m, 2H), 3.20-3.15 (m, 2H), 2.58-2.55 (m, 2H), 2.27-2.15 (m, 2H), 1.921-1.920 (m, 3H), 1.85-1.74 (m, 2H), 1.56-1.38 (m, 8H), 1.24-1.18 (m, 24H), 1.14-1.11 (m, 10H), 1.00-0.98 (m, 14H), 0.82 (t, 6H, J=7.6 Hz); $^{13}$C NMR (100 MHz, CDCl$_3$) δ 173.6, 168.6, 140.5, 119.2, 117.7, 79.1, 61.7, 61.5, 61.1, 61.0, 58.7, 58.5, 43.4, 43.3, 39.9, 39.7, 35.6, 34.2, 31.9, 31.1, 29.8, 29.71, 29.67, 29.59, 29.50, 29.46, 27.1, 24.8, 24.74, 24.69, 24.66, 20.55, 20.49, 18.9, 18.1, 17.9, 14.4, 14.1, 13.6, 8.53; $^{31}$P NMR (162 MHz, CDCl$_3$) δ 149.9.

Example 7

Synthesis, Cleavage and Deprotection of ODN 16

Figure 12:
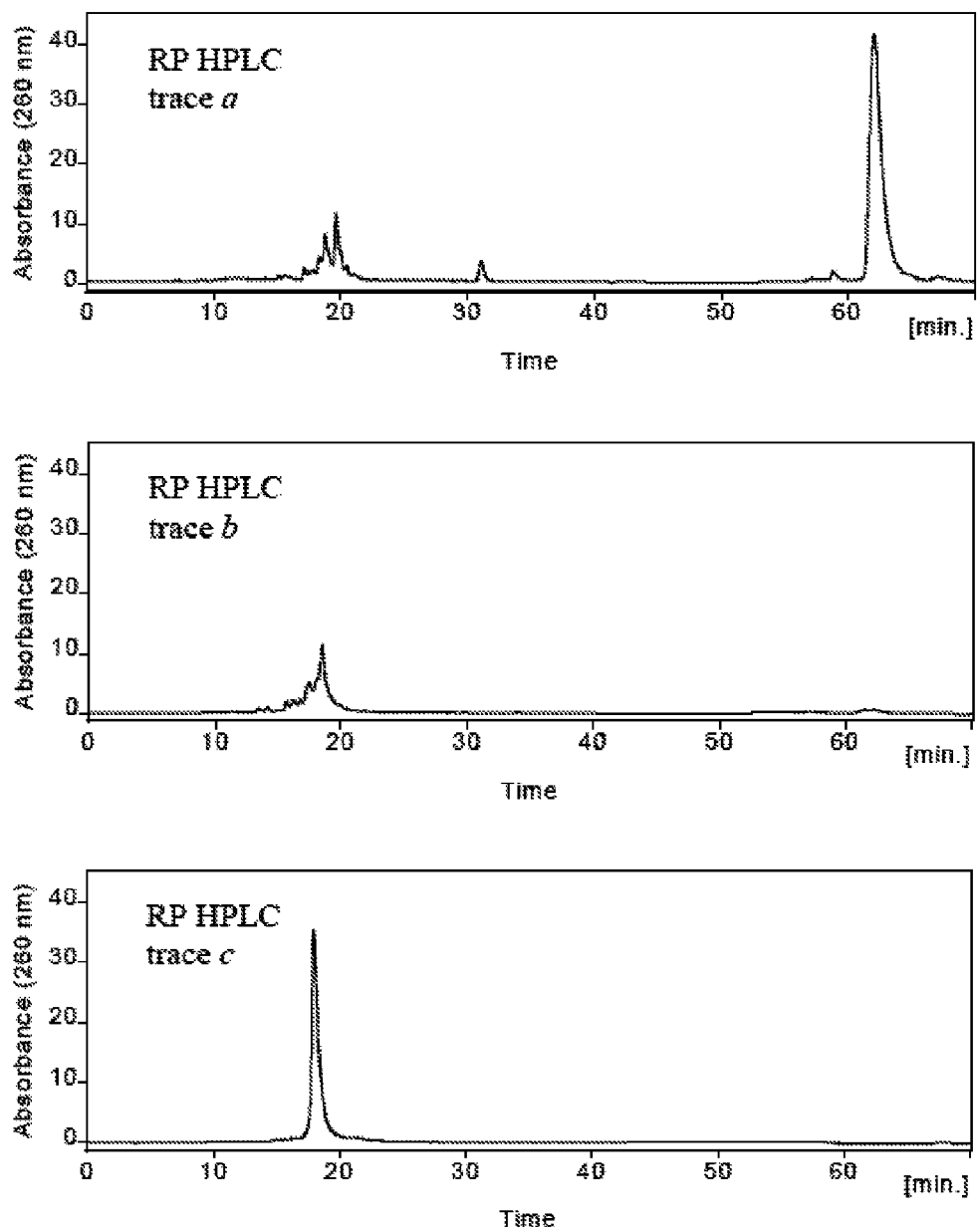
FIG. 12 depicts reverse-phase HPLC traces of oligodeoxynucleotide samples from the exemplary purification method illustrated in FIG. 11 (a) crude ODN that contains full-length sequence 4 and failure ones 5; (b) failure sequences 5 removed from polymer; (c) 5'-phosphorylated ODN 8 purified through catching by polymerization.
Figure 13:
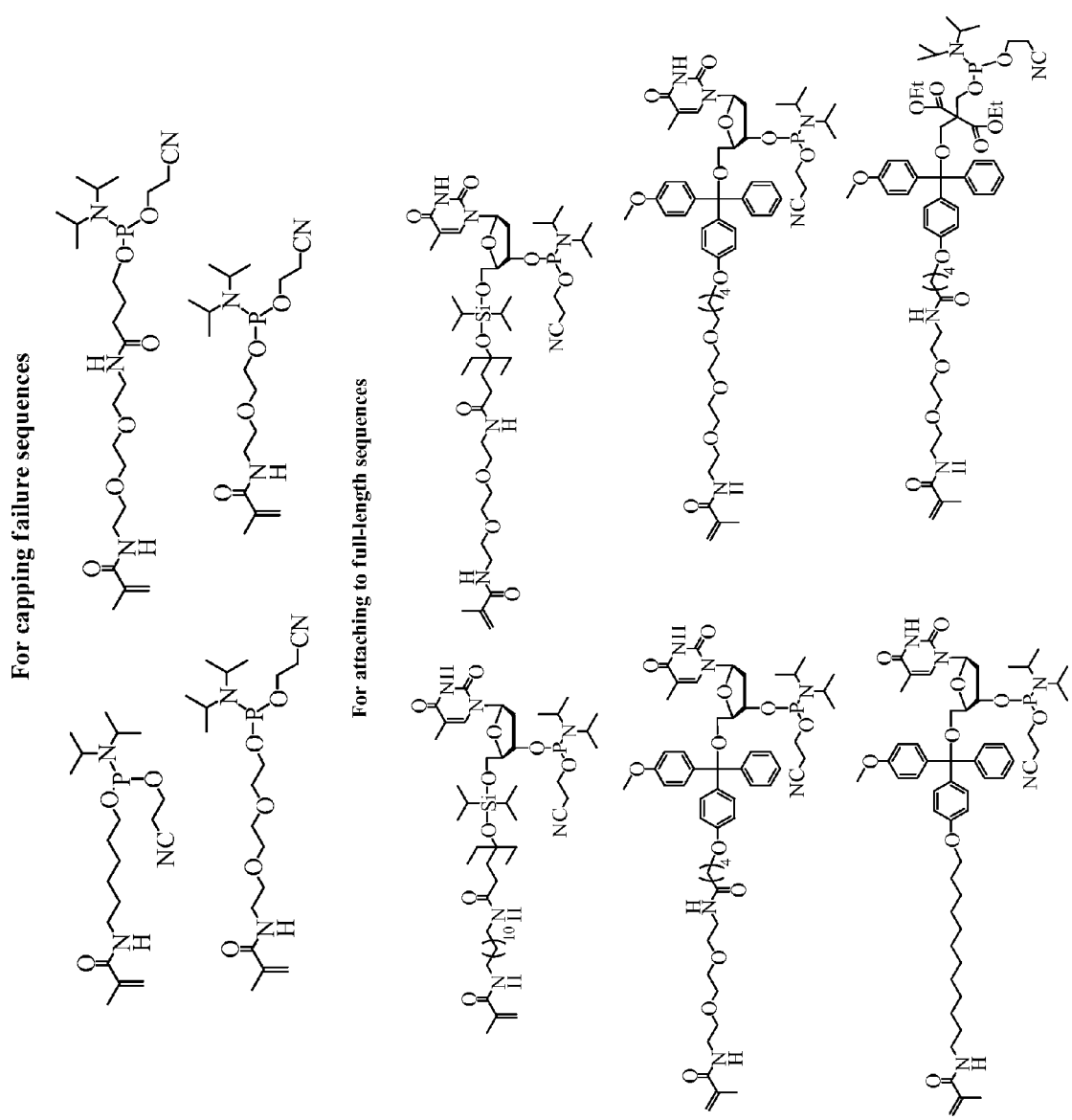
FIG. 13 depicts compounds useful in the present invention.

The 20-mer 5'-acrylated and phosphorylated ODN 16 was synthesized on an ABI DNA/RNA synthesizer at 1 µmol scale. The solid support was lcaa-CPG. The ODN was anchored to the support through a succinic ester linkage. The following 5'-DMTr-protected 2-cyanoethyl phosphoramidite monomers were used for the synthesis: Pac-dA, 4-isopropyl-Pac-dG, Ac-dC and dT. THF/pyridine/Pac$_2$O was used as the capping reagent. The manufacturer recommended synthetic cycle was followed except that the phosphoramidite 13 was coupled for min. After synthesis, the ODN 16 was cleaved from CPG with concentrated NH$_4$OH at room temperature for 8 hours on the synthesizer. The solution of crude ODN 16 was divided into 10 equal portions, and evaporated to dryness in 10 Eppendorf tubes in a vacuum SpeedVac concentrator. One portion was dissolved in 150 µL water, of which 20 µL was injected into HPLC to generate trace a (FIG. 12).

Polymerization of Full-Length ODN.

The remaining 130 µL solution of the crude ODN 16 was transferred to a 2-necked round-bottomed flask. The Eppendorf tube was washed with water (40 µL×3) and the washes were added to the flask. A polymerization solution [250 µL; dimethylacrylamide (1.69 M) and N,N'-methylenebis(acrylamide) (16.9 mM) in water; the solution can be pre-prepared and stored at −20° C. in dark for at least 1 month] was added via a pipette. The mixture was gently stirred under a nitrogen flow for 2 minutes. The solution of (NH$_4$)$_2$S$_2$O$_4$ (10%, 5 µL) was then added via a pipette, which was followed by N,N,N',N'-tetramethylethylenediamine (TMEDA, 5 µL). The mixture was stirred gently under nitrogen at room temperature for 30 minutes. The ODN-polyacrylamide conjugate 18 was formed. The failure sequences 17 remained in solution (FIG.

11). The gel was allowed to stand for another 30 minutes to ensure complete polymerization.

Removal of Failure Sequences and Other Impurities.

To the ODN-polymer conjugate 18 in the round-bottomed flask was added 3 mL water. The content was gently shaken at room temperature overnight. The supernatant, which contained the failure sequences 17 and other impurities, was removed with a pipette. The gel was further washed with water (2 mL×3; 2 hours each time). The supernatant and the washes were combined and evaporated to dryness. The residue was dissolved in 130 μL water, of which μL was injected into HPLC to generate profile b (FIG. 12).

Cleavage of Full-Length ODN from Polymer and Releasing the 5'-Phosphate Group.

Figure 11:
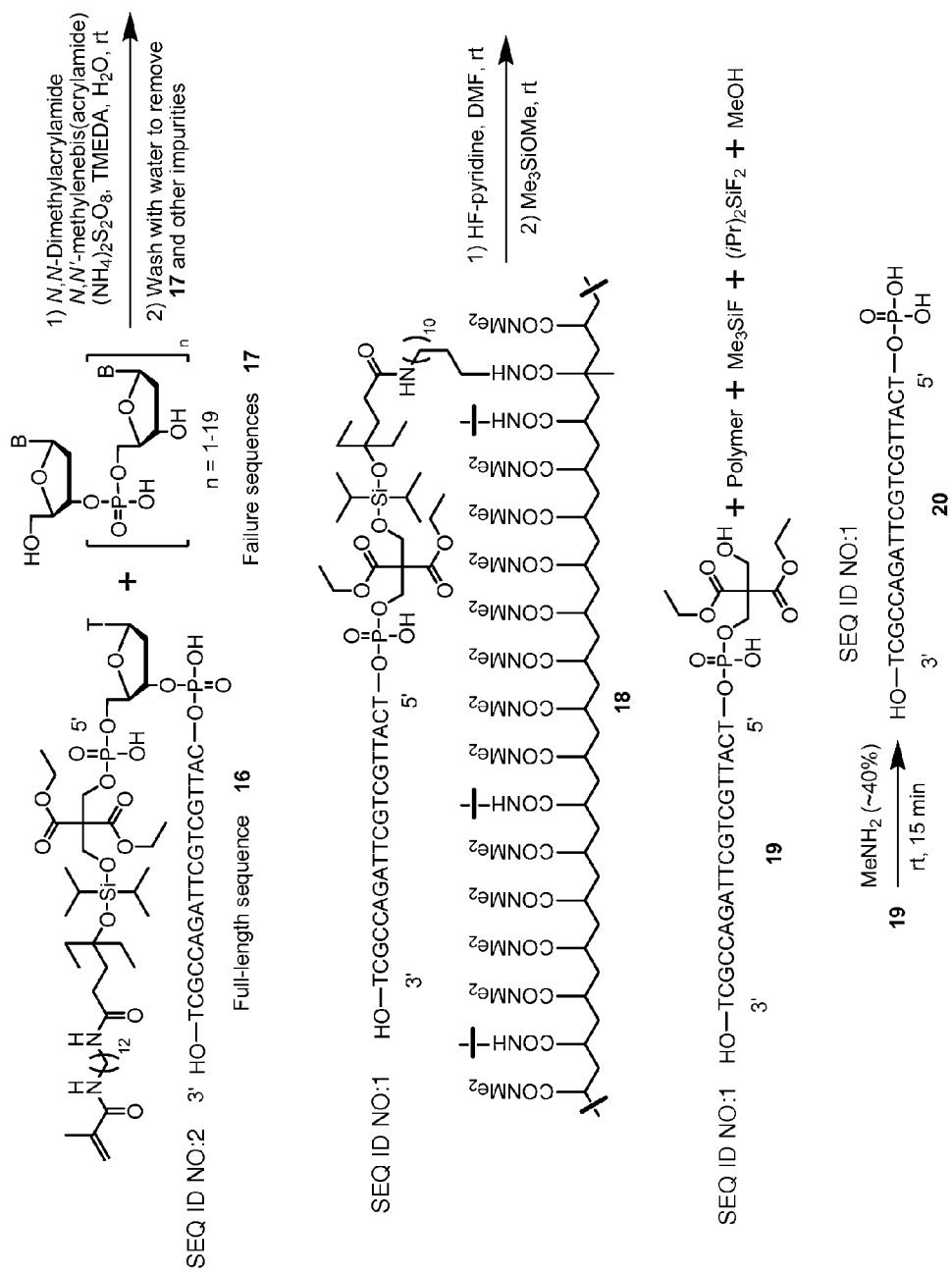
FIG. 11 illustrates an exemplary method of the invention, used to purify an exemplary oligodeoxynucleotide 20.

The gel in the round-bottomed flask was dried under vacuum. Dry DMF (2 mL) was added via a pipette, which was followed by HF-pyridine complex (60 μL). The mixture was shaken gently under nitrogen for 5 hours. $Me_3SiOMe$ (500 μL) was then added. After shaking for 15 minutes, the supernatant was transferred to Eppendorf tubes. The gel was extracted with water (2 mL×3 at rt; 12 hours, 2 hours, 2 hours, respectively). The supernatant and the extracts were evaporated to dryness in a SpeedVac vacuum concentrator and were combined to give ODN 19 (FIG. 11). To deprotect the 5'-phosphate group of 19, concentrated $MeNH_2$ (~40%, 100 μL) was added. After a short vortex, the mixture was allowed to stand at room temperature for minutes. nBuOH (900 μL) was added. The mixture was vortexed for 30 seconds and then centrifuged at 14.5K for 5 minutes. The supernatant was removed. The residue was further dried shortly in a SpeedVac. The ODN 20 was dissolved in 130 μL water, of which 20 μL was injected into HPLC to generate profile c (FIG. 12). The recovery yield of the purification process was estimated to be 55% by comparing the area of the peak in trace c at 19 min with that in trace a at 62 min. MALDI-TOF mass spectrum of ODN 20 calcd for $[M-2H+Na]^-$ $C_{194}H_{247}N_{67}NaO_{125}P_{20}$ 6159.0. found 6159.8.

All patents, publications and references cited herein are hereby fully incorporated by reference. In case of conflict between the present disclosure and incorporated patents, publications and references, the present disclosure should control.

The invention claimed is:

1. A method of purifying an oligonucleotide comprising:

reacting a full length oligonucleotide with a compound of formula (IIe), to attach a polymerizable functional group to an end of the full length oligonucleotide;

polymerizing the full length oligonucleotides;

removing the failure sequences from the polymerized full length oligonucleotides; and recovering the full length oligonucleotides, wherein the compound of formula (IIe) is:

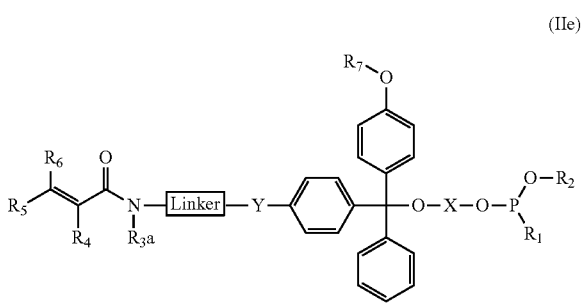

(IIe)

wherein:

X is selected from:

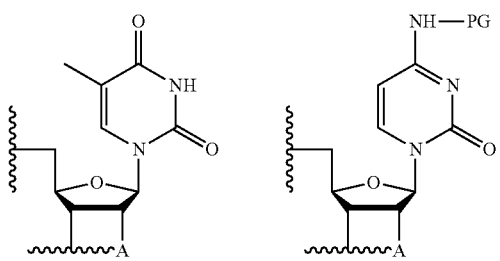

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
tcattgctgc ttagaccgct                                           20

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
cattgctgct tagaccgct                                            19

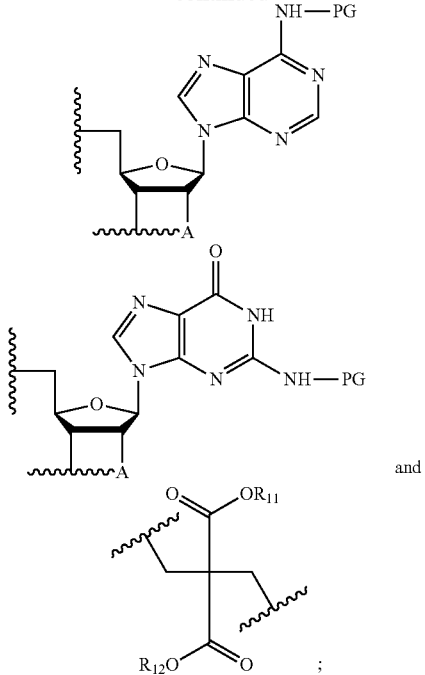

and

R₁ is halo or —NR_aR_b;

R₂ is —CH₃ or —CH₂—CH₂-EWG;

EWG is an electron-withdrawing group;

$R_{3a}$, $R_{3b}$, $R_4$, $R_5$, $R_6$ and $R_{20}$ are each independently hydrogen or alkyl;

$R_7$, $R_8$, $R_9$, $R_{10}$, $R_{11}$, $R_{12}$, $R_a$ and $R_b$ are each independently alkyl;

each A is independently selected from hydrogen and —O-PG;

each PG is independently selected from hydrogen and a protecting group;

Y is —O—, —CH₂—, —S—, —C(=O)N(R₂₀)—, —N(R₂₀)C(=O)— or —N(R₂₀)— linker is (CH₂)_r or (CH₂)_x[(CH₂)_xO(CH₂)_x]_p(CH₂)_y or (CH₂)_x[(CH₂)_xO(CH₂)_x]_n(CH₂)_xN(R')C(=O)(CH₂)_m or (CH₂)_rN(R')C(=O)(CH₂)_m or;

each x and y are independently an integer from 1 to 12;

r is an integer from 1 to 36;

p is an integer from 1 to 18; and m is an integer from 1 to 18.

2. The method of claim 1, wherein $R_{3a}$ is hydrogen.

3. The method of claim 1, wherein Y is —O—.

4. The method of claim 1, wherein the compound of formula (IIe) is:

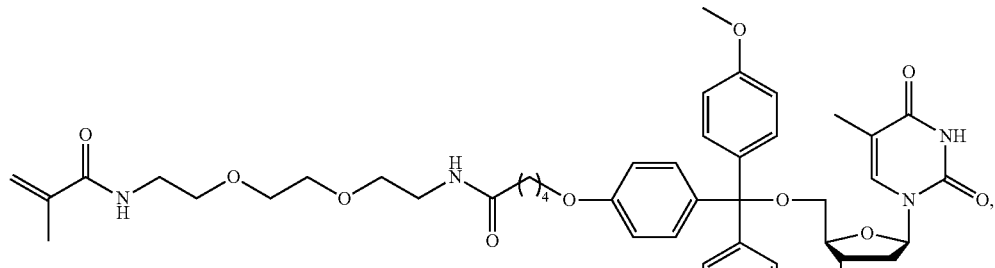

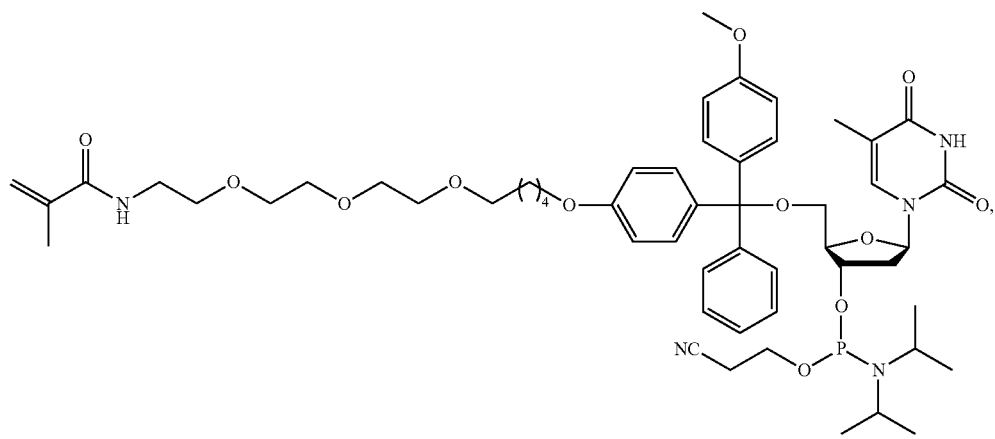

-continued
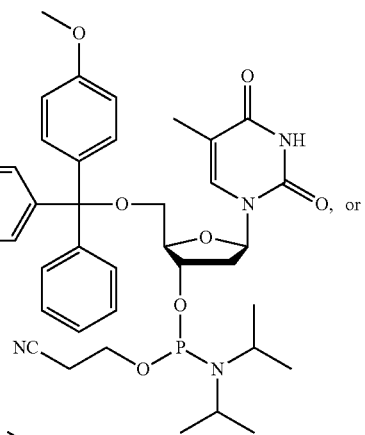
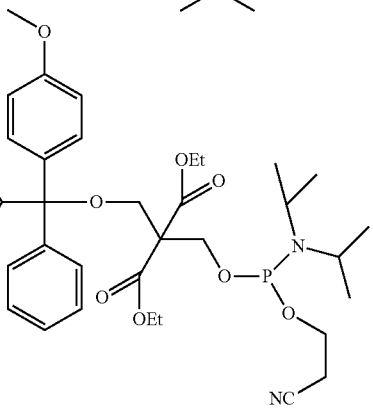
5. A compound selected from the group consisting of:
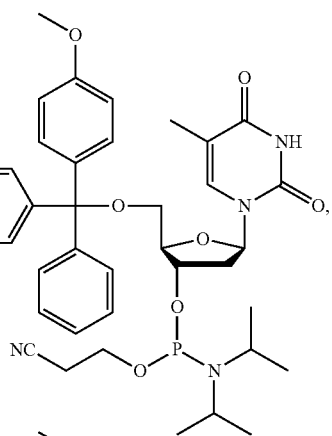
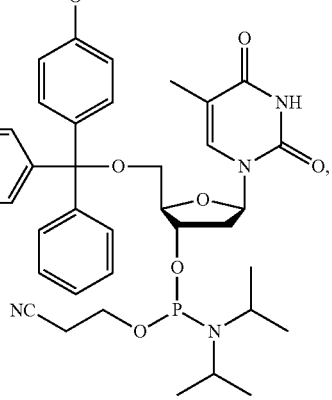

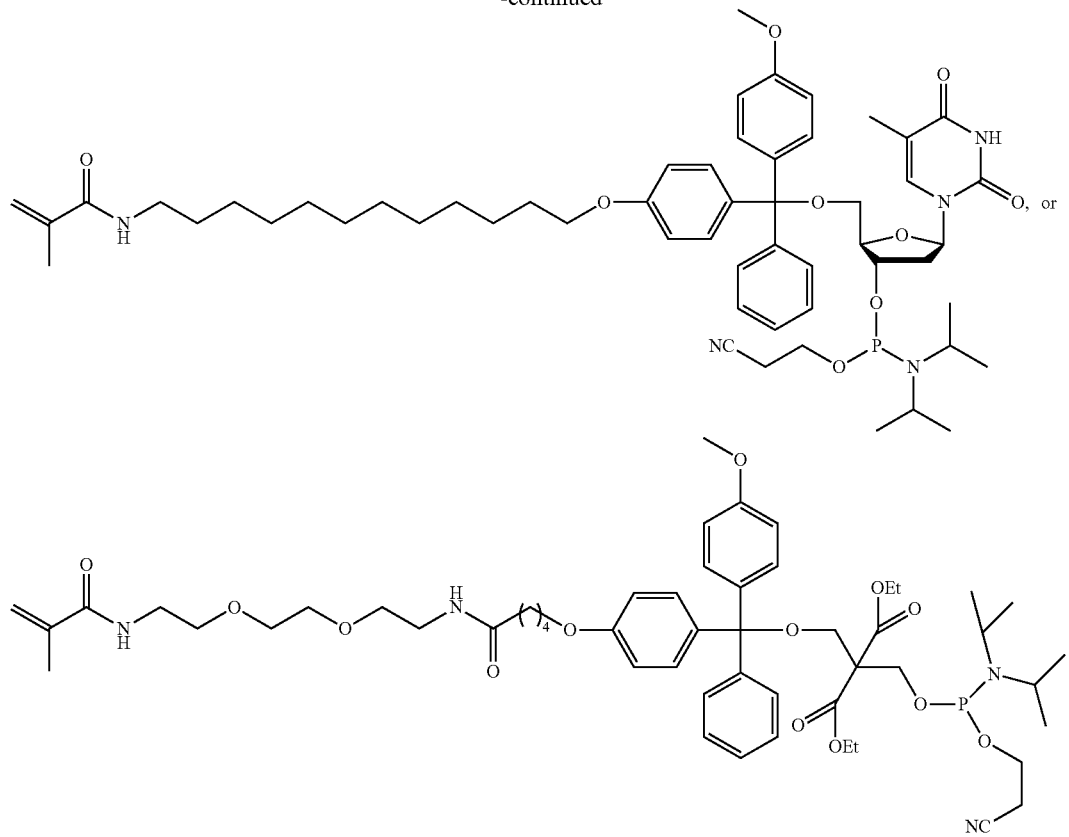
6. A kit for purifying oligonucleotides comprising a compound of formula (IIe); wherein the compound of formula (IIe) is:
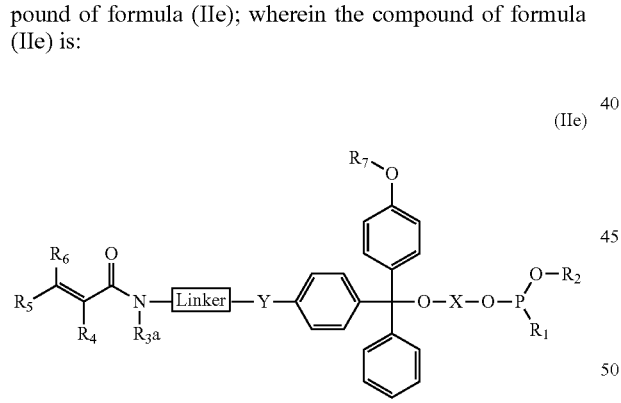
(IIe)
wherein:
X is selected from:
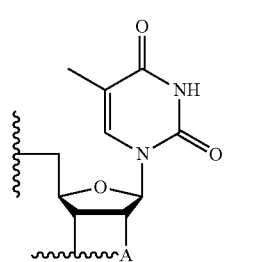 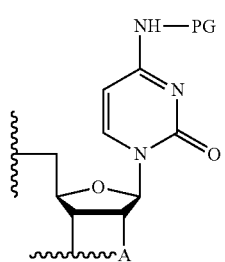
-continued
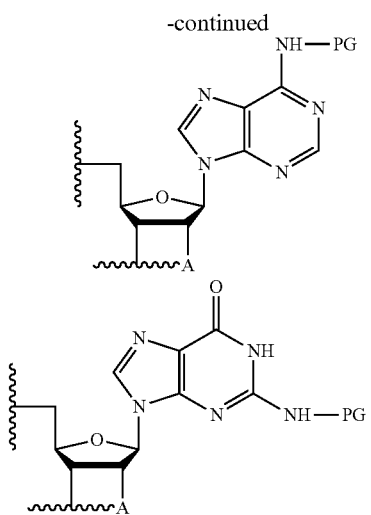
and
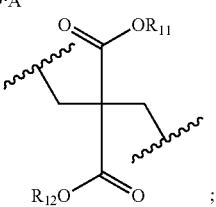
;
$R_1$ is halo or —$NR_aR_b$;
$R_2$ is —$CH_3$ or —$CH_2$—$CH_2$-EWG;
EWG is an electron-withdrawing group;

$R_{3a}$, $R_{3b}$, $R_4$, $R_5$, $R_6$ and $R_{20}$ are each independently hydrogen or alkyl;

$R_7$, $R_8$, $R_9$, $R_{10}$, $R_{11}$, $R_{12}$, $R_a$ and $R_b$ are each independently alkyl;

each A is independently selected from hydrogen and —O-PG;

each PG is independently selected from hydrogen and a protecting group;

Y is —O—, —CH$_2$—, —S—, —C(═O)N(R$_{20}$)—, —N(R$_{20}$)C(═O)— or —N(R$_{20}$)— linker is (CH$_2$)$_r$ or (CH$_2$)$_x$[(CH$_2$)$_x$O(CH$_2$)$_x$]$_p$(CH$_2$)$_y$ or (CH$_2$)$_x$[(CH$_2$)$_x$O(CH$_2$)$_x$]$_n$(CH$_2$)$_x$N(R')C(═O)(CH$_2$)$_m$ or (CH$_2$)$_r$N(R')C(═O)(CH$_2$)$_m$ or;

each x and y are independently an integer from 1 to 12;

r is an integer from 1 to 36;

p is an integer from 1 to 18; and m is an integer from 1 to 18.

* * * * *